(12) United States Patent
Gounou et al.

(10) Patent No.: US 11,844,689 B2
(45) Date of Patent: Dec. 19, 2023

(54) ACHROMATIC LENSES AND LENSES HAVING DIFFRACTIVE PROFILES WITH IRREGULAR WIDTH FOR VISION TREATMENT

(71) Applicant: AMO GRONINGEN B.V., Groningen (NL)

(72) Inventors: Franck Gounou, Groningen (NL); Hendrik A. Weeber, Groningen (NL); Robert Rosen, Groningen (NL); Carmen Canovas Vidal, Groningen (NL); Patricia A. Piers, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 17/127,947

(22) Filed: Dec. 18, 2020

(65) Prior Publication Data
US 2021/0196452 A1    Jul. 1, 2021

Related U.S. Application Data

(60) Provisional application No. 62/955,355, filed on Dec. 30, 2019.

(51) Int. Cl.
*A61F 2/16* (2006.01)
*B29D 11/00* (2006.01)
*G16H 20/30* (2018.01)

(52) U.S. Cl.
CPC .......... *A61F 2/1656* (2013.01); *A61F 2/1624* (2013.01); *A61F 2/1637* (2013.01);
(Continued)

(58) Field of Classification Search
CPC .............................. A61F 2/1654; A61F 2/1656
See application file for complete search history.

(56) References Cited

U.S. PATENT DOCUMENTS

| 3,367,734 A | 2/1968 | Karl et al. |
| 3,722,986 A | 3/1973 | Tagnon |

(Continued)

FOREIGN PATENT DOCUMENTS

| AU | 2005230194 B2 | 12/2010 |
| CA | 2501217 A1 | 4/2004 |

(Continued)

OTHER PUBLICATIONS

International Search Report and Written Opinion for Application No. PCT/EP2019/083615, dated Mar. 17, 2020, 14 pages.

(Continued)

*Primary Examiner* — Javier G Blanco
(74) *Attorney, Agent, or Firm* — Johnson & Johnson Surgical Vision, Inc.

(57) ABSTRACT

Apparatuses, systems and methods for providing improved ophthalmic lenses, particularly intraocular lenses (IOLs), include features for providing improved extended depth of focus lenses. Exemplary ophthalmic lenses can include an optic including a diffractive profile including at least one set of echelettes, each echelette of the set having a different width in r-squared space than any other echelette of the set and the at least one set of echelettes repeating at least once upon the optic.

12 Claims, 8 Drawing Sheets

(52) U.S. Cl.
CPC ...... *A61F 2/1654* (2013.01); *B29D 11/00269* (2013.01); *B29D 11/00961* (2013.01); *G16H 20/30* (2018.01); *A61F 2240/002* (2013.01); *G05B 2219/2617* (2013.01)

(56) References Cited

U.S. PATENT DOCUMENTS

| | | |
|---|---|---|
| 4,210,391 A | 7/1980 | Cohen et al. |
| 4,340,283 A | 7/1982 | Cohen |
| 4,460,275 A | 7/1984 | Spriggs |
| 4,504,892 A | 3/1985 | Zulfilar |
| 4,504,982 A | 3/1985 | Burk |
| 4,580,883 A | 4/1986 | Shinohara |
| 4,606,626 A | 8/1986 | Shinohara |
| 4,637,697 A | 1/1987 | Freeman |
| 4,640,593 A | 2/1987 | Shinohara |
| 4,641,934 A | 2/1987 | Freeman |
| 4,642,112 A | 2/1987 | Freeman |
| 4,655,565 A | 4/1987 | Freeman |
| 4,710,193 A | 12/1987 | Volk |
| 4,762,408 A | 8/1988 | Shinohara |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,856,234 A | 8/1989 | Goins |
| 4,856,889 A | 8/1989 | Guilino et al. |
| 4,881,804 A | 11/1989 | Cohen |
| 4,881,805 A | 11/1989 | Cohen |
| 4,898,461 A | 2/1990 | Portney |
| 4,932,970 A | 6/1990 | Portney |
| 4,936,666 A | 6/1990 | Futhey |
| 4,957,506 A | 9/1990 | Mercier |
| 4,978,211 A | 12/1990 | Cornu et al. |
| 4,995,714 A | 2/1991 | Cohen |
| 4,995,715 A | 2/1991 | Cohen |
| 5,016,977 A | 5/1991 | Baude et al. |
| 5,017,000 A | 5/1991 | Cohen |
| 5,019,098 A | 5/1991 | Mercier |
| 5,050,981 A | 9/1991 | Roffman |
| 5,054,905 A | 10/1991 | Cohen |
| 5,056,908 A | 10/1991 | Cohen |
| 5,061,058 A | 10/1991 | Guilino et al. |
| 5,066,301 A | 11/1991 | Wiley |
| 5,076,684 A | 12/1991 | Simpson et al. |
| 5,089,023 A | 2/1992 | Swanson |
| 5,089,024 A | 2/1992 | Christie et al. |
| 5,096,285 A | 3/1992 | Silberman |
| 5,100,226 A | 3/1992 | Freeman |
| 5,104,212 A | 4/1992 | Taboury et al. |
| 5,112,351 A | 5/1992 | Christie et al. |
| 5,114,220 A | 5/1992 | Baude et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,148,205 A | 9/1992 | Guilino et al. |
| 5,161,057 A | 11/1992 | Johnson |
| 5,173,723 A | 12/1992 | Volk et al. |
| 5,178,636 A | 1/1993 | Silberman |
| 5,191,366 A | 3/1993 | Kashiwagi |
| 5,220,359 A | 6/1993 | Roffman |
| 5,225,858 A | 7/1993 | Portney |
| 5,229,797 A | 7/1993 | Futhey et al. |
| 5,236,970 A | 8/1993 | Christ et al. |
| 5,257,132 A | 10/1993 | Ceglio et al. |
| 5,260,727 A | 11/1993 | Oksman et al. |
| 5,322,649 A | 6/1994 | Rheinish et al. |
| 5,344,447 A | 9/1994 | Swanson |
| 5,349,394 A | 9/1994 | Freeman et al. |
| 5,349,471 A | 9/1994 | Morris et al. |
| 5,381,190 A | 1/1995 | Rehse et al. |
| 5,384,606 A | 1/1995 | Koch et al. |
| 5,408,281 A | 4/1995 | Zhang |
| 5,443,506 A | 8/1995 | Garabet |
| 5,443,507 A | 8/1995 | Jacobi |
| 5,444,106 A | 8/1995 | Zhou et al. |
| 5,446,508 A | 8/1995 | Kitchen |
| 5,448,312 A | 9/1995 | Roffman et al. |
| 5,485,228 A | 1/1996 | Roffman et al. |
| 5,581,405 A | 12/1996 | Meyers et al. |
| 5,589,982 A | 12/1996 | Faklis et al. |
| 5,629,800 A | 5/1997 | Hamblen |
| 5,652,638 A | 7/1997 | Roffman et al. |
| 5,674,284 A | 10/1997 | Chang et al. |
| 5,682,223 A | 10/1997 | Menezes et al. |
| 5,683,457 A | 11/1997 | Gupta et al. |
| 5,684,560 A | 11/1997 | Roffman et al. |
| 5,684,595 A | 11/1997 | Kato et al. |
| 5,699,142 A | 12/1997 | Lee et al. |
| 5,715,031 A | 2/1998 | Roffman et al. |
| 5,715,091 A | 2/1998 | Meyers |
| 5,724,258 A | 3/1998 | Roffman |
| 5,728,156 A | 3/1998 | Gupta et al. |
| 5,748,282 A | 5/1998 | Freeman |
| 5,760,871 A | 6/1998 | Kosoburd et al. |
| 5,777,719 A | 7/1998 | Williams et al. |
| 5,796,462 A | 8/1998 | Roffman et al. |
| 5,800,532 A | 9/1998 | Lieberman |
| 5,805,260 A | 9/1998 | Roffman et al. |
| 5,822,091 A | 10/1998 | Baker |
| 5,838,496 A | 11/1998 | Maruyama et al. |
| 5,847,802 A | 12/1998 | Menezes et al. |
| 5,888,122 A | 3/1999 | Gupta et al. |
| 5,895,422 A | 4/1999 | Hauber |
| 5,895,610 A | 4/1999 | Chang et al. |
| 5,929,969 A | 7/1999 | Roffman |
| 5,968,094 A | 10/1999 | Werblin et al. |
| 5,968,095 A | 10/1999 | Norrby |
| 5,982,543 A | 11/1999 | Fiala |
| 6,007,747 A | 12/1999 | Blake et al. |
| 6,019,472 A | 2/2000 | Koester et al. |
| 6,050,687 A | 4/2000 | Bille et al. |
| 6,070,980 A | 6/2000 | Obara et al. |
| 6,082,856 A | 7/2000 | Dunn et al. |
| 6,086,204 A | 7/2000 | Magnante |
| 6,089,711 A | 7/2000 | Blankenbecler et al. |
| 6,095,651 A | 8/2000 | Williams et al. |
| 6,120,148 A | 9/2000 | Fiala et al. |
| 6,126,283 A | 10/2000 | Wen et al. |
| 6,126,286 A | 10/2000 | Portney |
| 6,139,145 A | 10/2000 | Israel |
| 6,142,625 A | 11/2000 | Sawano et al. |
| 6,145,987 A | 11/2000 | Baude et al. |
| 6,154,323 A | 11/2000 | Kamo |
| 6,199,986 B1 | 3/2001 | Williams et al. |
| 6,210,005 B1 | 4/2001 | Portney |
| 6,215,096 B1 | 4/2001 | Von Wallfeld et al. |
| 6,224,211 B1 | 5/2001 | Gordon |
| 6,231,603 B1 | 5/2001 | Lang et al. |
| 6,270,220 B1 | 8/2001 | Keren |
| 6,271,915 B1 | 8/2001 | Frey et al. |
| 6,325,510 B1 | 12/2001 | Golub et al. |
| 6,338,559 B1 | 1/2002 | Williams et al. |
| 6,353,503 B1 | 3/2002 | Spitzer et al. |
| 6,413,276 B1 | 7/2002 | Werblin |
| 6,429,972 B1 | 8/2002 | Ota et al. |
| 6,439,720 B1 | 8/2002 | Graves et al. |
| 6,457,826 B1 | 10/2002 | Lett |
| 6,462,874 B1 | 10/2002 | Soskind |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,497,483 B2 | 12/2002 | Frey et al. |
| 6,511,180 B2 | 1/2003 | Guirao et al. |
| 6,520,638 B1 | 2/2003 | Roffman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |

(56) References Cited

U.S. PATENT DOCUMENTS

| | | |
|---|---|---|
| 6,547,391 B2 | 4/2003 | Ross, III et al. |
| 6,547,822 B1 | 4/2003 | Lang |
| 6,554,425 B1 | 4/2003 | Roffman et al. |
| 6,554,859 B1 | 4/2003 | Lang et al. |
| 6,557,992 B1 | 5/2003 | Dwyer et al. |
| 6,576,012 B2 | 6/2003 | Lang |
| 6,582,076 B1 | 6/2003 | Roffman et al. |
| 6,585,375 B2 | 7/2003 | Donitzky et al. |
| 6,609,673 B1 | 8/2003 | Johnson |
| 6,609,793 B2 | 8/2003 | Norrby et al. |
| 6,616,275 B1 | 9/2003 | Dick et al. |
| 6,655,802 B2 | 12/2003 | Zimmermann et al. |
| 6,685,315 B1 | 2/2004 | De |
| 6,705,729 B2 | 3/2004 | Piers et al. |
| 6,709,103 B1 | 3/2004 | Roffman et al. |
| 6,755,524 B2 | 6/2004 | Rubinstein et al. |
| 6,791,754 B2 | 9/2004 | Ogawa |
| 6,802,605 B2 | 10/2004 | Cox et al. |
| 6,808,262 B2 | 10/2004 | Chapoy et al. |
| 6,818,158 B2 | 11/2004 | Pham et al. |
| 6,827,444 B2 | 12/2004 | Williams et al. |
| 6,830,332 B2 | 12/2004 | Piers et al. |
| 6,835,204 B1 | 12/2004 | Stork et al. |
| 6,846,326 B2 | 1/2005 | Zadno-Azizi et al. |
| 6,848,790 B1 | 2/2005 | Dick et al. |
| 6,851,803 B2 | 2/2005 | Wooley et al. |
| 6,884,261 B2 | 4/2005 | Zadno-Azizi et al. |
| 6,923,539 B2 | 8/2005 | Simpson et al. |
| 6,923,540 B2 | 8/2005 | Ye et al. |
| 6,951,391 B2 | 10/2005 | Morris et al. |
| 6,957,891 B2 | 10/2005 | Fiala |
| 6,972,032 B2 | 12/2005 | Aharoni et al. |
| 6,986,578 B2 | 1/2006 | Jones |
| 7,025,456 B2 | 4/2006 | Morris et al. |
| 7,036,931 B2 | 5/2006 | Lindacher et al. |
| 7,048,759 B2 | 5/2006 | Bogaert et al. |
| 7,048,760 B2 | 5/2006 | Cumming |
| 7,061,693 B2 | 6/2006 | Zalevsky |
| 7,073,906 B1 | 7/2006 | Portney |
| 7,093,938 B2 | 8/2006 | Morris et al. |
| 7,111,938 B2 | 9/2006 | Andino et al. |
| 7,137,702 B2 | 11/2006 | Piers et al. |
| 7,156,516 B2 | 1/2007 | Morris et al. |
| 7,159,983 B2 | 1/2007 | Menezes et al. |
| 7,188,949 B2 | 3/2007 | Bandhauer et al. |
| 7,198,640 B2 | 4/2007 | Nguyen |
| 7,217,375 B2 | 5/2007 | Lai |
| 7,221,513 B2 | 5/2007 | Cho et al. |
| 7,232,218 B2 | 6/2007 | Morris et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,377,641 B2 | 5/2008 | Piers et al. |
| 7,441,894 B2 | 10/2008 | Zhang et al. |
| 7,455,404 B2 | 11/2008 | Bandhauer et al. |
| 7,475,986 B2 | 1/2009 | Dai et al. |
| 7,481,532 B2 | 1/2009 | Hong et al. |
| 7,543,937 B2 | 6/2009 | Piers et al. |
| 7,572,007 B2 | 8/2009 | Simpson |
| 7,604,350 B2 | 10/2009 | Dursteler et al. |
| 7,615,073 B2 | 11/2009 | Deacon et al. |
| 7,654,667 B2 | 2/2010 | Blum et al. |
| 7,670,371 B2 | 3/2010 | Piers et al. |
| 7,677,725 B2 | 3/2010 | Piers et al. |
| 7,717,558 B2 | 5/2010 | Hong et al. |
| 7,753,521 B2 | 7/2010 | Wooley et al. |
| 7,871,162 B2 | 1/2011 | Weeber |
| 7,883,207 B2 | 2/2011 | Iyer et al. |
| 7,896,916 B2 | 3/2011 | Piers et al. |
| 7,922,326 B2 | 4/2011 | Bandhauer et al. |
| 7,984,990 B2 | 7/2011 | Bandhauer et al. |
| 7,998,198 B2 | 8/2011 | Angelopoulos et al. |
| 8,128,222 B2 | 3/2012 | Portney |
| 8,157,374 B2 | 4/2012 | Bandhauer et al. |
| 8,192,022 B2 | 6/2012 | Zalevsky |
| 8,197,063 B2 | 6/2012 | Iyer et al. |
| 8,216,307 B2 | 7/2012 | Schaper, Jr. |
| 8,231,219 B2 | 7/2012 | Weeber |
| 8,231,673 B2 | 7/2012 | Sacharoff et al. |
| 8,235,525 B2 | 8/2012 | Lesage et al. |
| 8,240,850 B2 | 8/2012 | Apter et al. |
| 8,262,728 B2 | 9/2012 | Zhang et al. |
| 8,292,953 B2 | 10/2012 | Weeber et al. |
| 8,382,281 B2 | 2/2013 | Weeber |
| 8,388,137 B2 | 3/2013 | Dreher et al. |
| 8,444,267 B2 | 5/2013 | Weeber et al. |
| 8,480,228 B2 | 7/2013 | Weeber |
| 8,500,805 B2 | 8/2013 | Kobayashi et al. |
| 8,506,075 B2 | 8/2013 | Bandhauer et al. |
| 8,529,623 B2 | 9/2013 | Piers et al. |
| 8,556,416 B2 | 10/2013 | Lawu |
| 8,556,417 B2 | 10/2013 | Das et al. |
| 8,573,775 B2 | 11/2013 | Weeber |
| 8,619,362 B2 | 12/2013 | Portney |
| 8,636,796 B2 | 1/2014 | Houbrechts et al. |
| 8,652,205 B2 | 2/2014 | Hong et al. |
| 8,678,583 B2 | 3/2014 | Cohen |
| 8,709,079 B2 | 4/2014 | Zhang et al. |
| 8,734,511 B2 | 5/2014 | Weeber et al. |
| 8,740,978 B2 | 6/2014 | Weeber et al. |
| 8,747,466 B2 | 6/2014 | Weeber et al. |
| 8,755,117 B2 | 6/2014 | Kobayashi et al. |
| 8,771,348 B2 | 7/2014 | Zhao |
| 8,827,446 B2 | 9/2014 | Iyer et al. |
| 8,906,089 B2 | 12/2014 | Piers et al. |
| 9,069,185 B2 | 6/2015 | Zhao |
| 9,078,745 B2 | 7/2015 | Zhang et al. |
| 9,122,074 B2 | 9/2015 | Piers et al. |
| 9,164,201 B2 | 10/2015 | Fermigier et al. |
| 9,223,148 B2 | 12/2015 | Fiala et al. |
| 9,304,329 B2 | 4/2016 | Zhao |
| 9,310,624 B2 | 4/2016 | Argal et al. |
| 9,320,594 B2 | 4/2016 | Schwiegerling |
| 9,329,309 B2 | 5/2016 | Van |
| 9,335,563 B2 | 5/2016 | Weeber |
| 9,335,564 B2 | 5/2016 | Choi et al. |
| 9,370,416 B2 | 6/2016 | Argal et al. |
| 9,518,864 B2 | 12/2016 | Grossinger et al. |
| 9,563,070 B2 | 2/2017 | Ando et al. |
| 9,622,856 B2 | 4/2017 | Weeber et al. |
| 9,869,580 B2 | 1/2018 | Grossinger et al. |
| 9,925,041 B2 | 3/2018 | Gerlach et al. |
| 2001/0018612 A1 | 8/2001 | Carson et al. |
| 2002/0082690 A1 | 6/2002 | Sarbadhikari |
| 2002/0093701 A1 | 7/2002 | Zhang et al. |
| 2002/0118337 A1 | 8/2002 | Perrott et al. |
| 2003/0014107 A1 | 1/2003 | Reynard |
| 2003/0076478 A1 | 4/2003 | Cox |
| 2003/0169491 A1 | 9/2003 | Bender et al. |
| 2003/0171808 A1 | 9/2003 | Phillips |
| 2004/0085515 A1 | 5/2004 | Roffman et al. |
| 2004/0088050 A1 | 5/2004 | Norrby et al. |
| 2004/0106992 A1 | 6/2004 | Lang et al. |
| 2004/0111153 A1 | 6/2004 | Woods et al. |
| 2004/0189981 A1 | 9/2004 | Ross et al. |
| 2005/0096226 A1 | 5/2005 | Stock et al. |
| 2005/0099589 A1 | 5/2005 | Ishak |
| 2005/0128432 A1 | 6/2005 | Altmann |
| 2005/0203619 A1 | 9/2005 | Altmann |
| 2005/0259222 A1 | 11/2005 | Kelch et al. |
| 2005/0267575 A1 | 12/2005 | Nguyen et al. |
| 2006/0004446 A1 | 1/2006 | Aharoni et al. |
| 2006/0009816 A1 | 1/2006 | Fang et al. |
| 2006/0030938 A1 | 2/2006 | Altmann |
| 2006/0066808 A1 | 3/2006 | Blum et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0139570 A1 | 6/2006 | Blum et al. |
| 2006/0238702 A1 | 10/2006 | Glick et al. |
| 2006/0244904 A1 | 11/2006 | Hong et al. |
| 2007/0052920 A1 | 3/2007 | Stewart et al. |
| 2007/0129803 A1 | 6/2007 | Cumming et al. |

(56) References Cited

U.S. PATENT DOCUMENTS

| | | |
|---|---|---|
| 2007/0171362 A1 | 7/2007 | Simpson et al. |
| 2007/0258143 A1 | 11/2007 | Portney |
| 2007/0268451 A1 | 11/2007 | Raghuprasad |
| 2007/0282438 A1 | 12/2007 | Hong et al. |
| 2008/0147185 A1 | 6/2008 | Hong et al. |
| 2008/0161913 A1 | 7/2008 | Brady et al. |
| 2008/0161914 A1 | 7/2008 | Brady et al. |
| 2008/0269891 A1 | 10/2008 | Hong et al. |
| 2008/0273169 A1 | 11/2008 | Blum et al. |
| 2008/0300679 A1 | 12/2008 | Altmann |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0240328 A1 | 9/2009 | Treushnikov et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0057202 A1 | 3/2010 | Bogaert |
| 2010/0087921 A1 | 4/2010 | Simpson |
| 2010/0131060 A1 | 5/2010 | Simpson et al. |
| 2010/0161051 A1 | 6/2010 | Hong |
| 2010/0274233 A1 | 10/2010 | Dick et al. |
| 2010/0281021 A1 | 11/2010 | Weeber et al. |
| 2010/0312336 A1 | 12/2010 | Hong et al. |
| 2011/0022170 A1 | 1/2011 | Simpson et al. |
| 2011/0109874 A1 | 5/2011 | Piers et al. |
| 2011/0125261 A1 | 5/2011 | Portney |
| 2011/0149236 A1 | 6/2011 | Weeber |
| 2011/0166652 A1 | 7/2011 | Bogaert et al. |
| 2011/0270596 A1 | 11/2011 | Weeber |
| 2011/0313522 A1 | 12/2011 | Hayes |
| 2011/0313523 A1 | 12/2011 | Hayes |
| 2011/0313525 A1 | 12/2011 | Cumming |
| 2012/0059464 A1 | 3/2012 | Zhao |
| 2012/0140166 A1 | 6/2012 | Zhao |
| 2012/0143326 A1 | 6/2012 | Canovas et al. |
| 2012/0154740 A1 | 6/2012 | Bradley et al. |
| 2012/0170121 A1 | 7/2012 | Okada et al. |
| 2012/0320335 A1 | 12/2012 | Weeber et al. |
| 2012/0323321 A1 | 12/2012 | Simonov et al. |
| 2013/0035760 A1 | 2/2013 | Portney |
| 2013/0046381 A1 | 2/2013 | Zalevsky et al. |
| 2013/0060330 A1 | 3/2013 | Weeber et al. |
| 2013/0107202 A1 | 5/2013 | Liang |
| 2015/0022775 A1 | 1/2015 | Ando et al. |
| 2015/0029460 A1 | 1/2015 | Bradley et al. |
| 2015/0094807 A1 | 4/2015 | Piers et al. |
| 2015/0359625 A1 | 12/2015 | Argal et al. |
| 2016/0216535 A1 | 7/2016 | Zhao |
| 2016/0220350 A1 | 8/2016 | Gerlach |
| 2016/0220352 A1 | 8/2016 | Choi et al. |
| 2016/0320633 A1 | 11/2016 | Weeber et al. |
| 2016/0334640 A1 | 11/2016 | De, Jr. et al. |
| 2016/0341978 A1 | 11/2016 | Schwiegerling |
| 2017/0209259 A1 | 7/2017 | Choi et al. |
| 2017/0216020 A1 | 8/2017 | Weeber et al. |
| 2017/0219846 A1 | 8/2017 | Ando |
| 2017/0227789 A1 | 8/2017 | Ando et al. |
| 2017/0239038 A1 | 8/2017 | Choi et al. |
| 2017/0245985 A1 | 8/2017 | Canovas et al. |
| 2017/0245986 A1 | 8/2017 | Canovas Vidal et al. |
| 2017/0245987 A1 | 8/2017 | Canovas et al. |
| 2017/0252151 A1 | 9/2017 | Mackool |
| 2018/0092739 A1 | 4/2018 | Pagnoulle et al. |
| 2018/0132996 A1 | 5/2018 | Tiwari et al. |
| 2018/0147050 A1 | 5/2018 | Choi et al. |
| 2018/0147052 A1 | 5/2018 | Hong et al. |
| 2018/0275428 A1 | 9/2018 | Ando |
| 2018/0368972 A1* | 12/2018 | Rosen .................. A61F 2/1627 |
| 2018/0373060 A1 | 12/2018 | Knox et al. |
| 2019/0224000 A1 | 7/2019 | Choi et al. |
| 2019/0254810 A1 | 8/2019 | Tiwari et al. |
| 2019/0307557 A1 | 10/2019 | De Carvalho et al. |
| 2019/0314148 A1 | 10/2019 | Liu |
| 2020/0038172 A1 | 2/2020 | Hussain et al. |
| 2021/0294123 A1 | 9/2021 | Weeber et al. |

FOREIGN PATENT DOCUMENTS

| | | |
|---|---|---|
| CA | 2507659 A1 | 6/2004 |
| CA | 2590085 A1 | 6/2006 |
| CN | 1951340 A | 4/2007 |
| CN | 104918580 A | 9/2015 |
| CN | 108646434 A | 10/2018 |
| EP | 335731 A2 | 10/1989 |
| EP | 342895 A2 | 11/1989 |
| EP | 0369561 A2 | 5/1990 |
| EP | 375291 A2 | 6/1990 |
| EP | 412751 A2 | 2/1991 |
| EP | 0457553 A2 | 11/1991 |
| EP | 470811 A2 | 2/1992 |
| EP | 605841 A1 | 7/1994 |
| EP | 0316162 B1 | 10/1995 |
| EP | 355230 B1 | 10/1995 |
| EP | 681198 A1 | 11/1995 |
| EP | 0537643 B1 | 3/1997 |
| EP | 949529 A2 | 10/1999 |
| EP | 1376203 A2 | 1/2004 |
| EP | 1862148 A1 | 12/2007 |
| EP | 1310267 B1 | 1/2008 |
| EP | 1891912 A1 | 2/2008 |
| EP | 2043558 A2 | 4/2009 |
| EP | 2045648 A1 | 4/2009 |
| EP | 1402308 B1 | 5/2009 |
| EP | 1424049 B1 | 6/2009 |
| EP | 2103279 A1 | 9/2009 |
| EP | 2113226 A1 | 11/2009 |
| EP | 2365379 A1 | 9/2011 |
| EP | 2377493 A1 | 10/2011 |
| EP | 2378319 A1 | 10/2011 |
| EP | 2290411 B1 | 5/2012 |
| EP | 2363097 B1 | 9/2012 |
| EP | 2812882 A1 | 12/2014 |
| EP | 2813881 A1 | 12/2014 |
| EP | 2349093 B1 | 10/2015 |
| EP | 3179293 A1 | 6/2017 |
| EP | 3150170 B1 | 12/2017 |
| EP | 3415980 A1 | 12/2018 |
| EP | 2527908 B1 | 3/2019 |
| IT | 1215851 B | 2/1990 |
| JP | 1154119 A | 6/1989 |
| JP | 2028615 A | 1/1990 |
| JP | 2079815 A | 3/1990 |
| JP | 2137814 A | 5/1990 |
| JP | 2249631 A | 10/1990 |
| JP | 3011315 A2 | 1/1991 |
| JP | 2013101323 A | 5/2013 |
| KR | 101154066 B1 | 6/2012 |
| WO | 9002963 A1 | 3/1990 |
| WO | 9222264 A1 | 12/1992 |
| WO | 9303409 A1 | 2/1993 |
| WO | 9413225 A1 | 6/1994 |
| WO | 9417435 A1 | 8/1994 |
| WO | 9724639 A1 | 7/1997 |
| WO | 9744689 A1 | 11/1997 |
| WO | 9831299 A2 | 7/1998 |
| WO | 9907309 A1 | 2/1999 |
| WO | 9923526 A1 | 5/1999 |
| WO | 0019906 A1 | 4/2000 |
| WO | 0076426 A2 | 12/2000 |
| WO | 0121061 A1 | 3/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 0234158 A2 | 5/2002 |
| WO | 02084381 A2 | 10/2002 |
| WO | 02088830 A1 | 11/2002 |
| WO | 03009053 A1 | 1/2003 |
| WO | 2004013680 A1 | 2/2004 |
| WO | 2004034129 A1 | 4/2004 |
| WO | 2004049979 A1 | 6/2004 |

(56) References Cited

FOREIGN PATENT DOCUMENTS

| | | | |
|---|---|---|---|
| WO | 2004090611 A2 | 10/2004 |
| WO | 2004096014 A2 | 11/2004 |
| WO | 2004113959 A2 | 12/2004 |
| WO | 05019906 A1 | 3/2005 |
| WO | 06025726 A1 | 3/2006 |
| WO | 2006047698 A1 | 5/2006 |
| WO | 06060477 A2 | 6/2006 |
| WO | 2006060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008150982 A1 | 12/2008 |
| WO | 2009017403 A1 | 2/2009 |
| WO | 2009027438 A2 | 3/2009 |
| WO | 2009043985 A1 | 4/2009 |
| WO | 2009058755 A1 | 5/2009 |
| WO | 2009076670 A1 | 6/2009 |
| WO | 2009130610 A2 | 10/2009 |
| WO | 2009148454 A1 | 12/2009 |
| WO | 2010046356 A1 | 4/2010 |
| WO | 2010054255 A1 | 5/2010 |
| WO | 2010059764 A1 | 5/2010 |
| WO | 2010079528 A1 | 7/2010 |
| WO | 2010093975 A2 | 8/2010 |
| WO | 2010100523 A1 | 9/2010 |
| WO | 2010104530 A1 | 9/2010 |
| WO | 2010144315 A1 | 12/2010 |
| WO | 2011024125 A1 | 3/2011 |
| WO | 2011055228 A2 | 5/2011 |
| WO | 2011075641 A2 | 6/2011 |
| WO | 2011075668 A1 | 6/2011 |
| WO | 2012004746 A2 | 1/2012 |
| WO | 2012031211 A1 | 3/2012 |
| WO | 2012070313 A1 | 5/2012 |
| WO | 2012078763 A1 | 6/2012 |
| WO | 2012085917 A1 | 6/2012 |
| WO | 2012122411 A1 | 9/2012 |
| WO | 2012140389 A1 | 10/2012 |
| WO | 2013018379 A1 | 2/2013 |
| WO | 2013028992 A1 | 2/2013 |
| WO | 2013093916 A1 | 6/2013 |
| WO | 2013114209 A2 | 8/2013 |
| WO | 2013116133 A1 | 8/2013 |
| WO | 2013113177 A1 | 8/2013 |
| WO | 2013118499 A1 | 8/2013 |
| WO | 2014008343 A1 | 1/2014 |
| WO | 2014033543 A2 | 3/2014 |
| WO | 2014091528 A1 | 6/2014 |
| WO | 2014111831 A1 | 7/2014 |
| WO | 2014189049 A1 | 11/2014 |
| WO | 2017137841 A1 | 8/2017 |
| WO | 2017149403 A1 | 9/2017 |
| WO | 2018093873 A1 | 5/2018 |
| WO | 2018150236 A1 | 8/2018 |
| WO | 2019002384 A1 | 1/2019 |
| WO | 2019130030 A1 | 7/2019 |
| WO | 2020115104 A1 | 6/2020 |

OTHER PUBLICATIONS

Morlock, R., et al., "Patient-Reported Spectacle Independence Questionnaire (PRSIQ): Development and Validation," American Journal of Ophthalmology, Jun. 2017, vol. 178, pp. 101-114.

Albert D.M., "(Book Review) Intraocular Lenses: Evolution, Designs, Complications, and Pathology, by David Apple et al.," Archieves of Opthalmology, 1990, vol. 108, pp. 650.

Alfonso J.F., et al., "Prospective Study of the Acri.LISA Bifocal Intraocular Lens," Journal of Cataract Refractive Surgery, Nov. 2007, vol. 33 (11), pp. 1930-1935.

Alvarez S. L. et al., "Spectral threshold: measurement and clinical applications," British Journal of Ophthalmology, 1983, 67, 504-507.

Apple D. J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.

Artal P., et al., "Contributions of the Cornea and the Lens to the Aberrations of the Human Eye," Optics Letters, 1998, vol. 23 (21), pp. 1713-1715.

Atchinson D.A., "Design of Aspheric Intraocular Lens," Ophthamic & Physiological Optics, 1991, vol. 11 (2), pp. 137-146.

Atchinson D.A., et al., "Optical Design of Intraocular Lenses. II. Off-Axis performance," Optometry & Vision Science, 1989, vol. 66 (9), pp. 579-590.

Atchinson D.A., et al., "Third-Order Aberrations Of Pseudophakic Eyes," Ophthalmic and Physiological Optics, 1989, vol. 9, pp. 205-211.

Atchinson D.A., "Optical Design of Intraocular Lenses. I. On-Axis Performance," American Academy of Optometry, 1989, vol. 66 (8), pp. 492-506.

Atchinson D.A., "Optical design of intraocular lenses III. On-Axis Performance in the Presence of Lens Displacement," American Academy of Optometry, 1989, vol. 66 (10), pp. 671-681.

Atchinson, "Refractive errors induced by displacement of intraocular lenses within the pseudophakic eye," Optometry & Vision Science, 1989, 66 (3), 146-152.

Bonnet R., et al., "New Method Of Topographical Ophthalmometry—Its Theoretical And Clinical Applications," American Journal of Optometry, 1962, vol. 39 (5), pp. 227-251.

Bradley A. et al., "Achromatizing the Human Eye" Optometry & Vision Science, 1991, vol. 68 (8), pp. 608-616.

Buralli D.A., et al., "Optical Performance Of Holographic Kinoforms," Applied Optics, Mar. 1989, vol. 28 (5), pp. 976-983.

Canovas C., et al., "Hybrid Adaptive-Optics Visual Simulator," Optical Letters, Jan. 15, 2010, vol. 35 (2), pp. 196-198.

Castignoles F., et al., "Comparison of the Efficiency, MTF and Chromatic Properties of Four Diffractive Bifocal Intraocular Lens Designs, " Optics Express, Mar. 2010, vol. 18 (5), pp. 5245-5256.

Cohen A.L., "Diffractive Bifocal Lens Design," Optometry and Vision Science, Jun. 1993, vol. 70 (6), pp. 461-468.

Cohen A.L., "Practical Design of a Bifocal Hologram Contact Lens or Intraocular Lens," Applied Optics, Jul. 1, 1992, vol. 31 (19), pp. 3750-3754.

Diffractive Lenses for Extended Depth of Focus and Presbyopic Correction, Presentation from Wavefront Congress field on Feb. 15, 2008, Rochester, New York.

Doskolovich L.L., et al., "Special Diffractive Lenses," Lens and Optical Systems Design, Apr. 1992, vol. 1780, pp. 393-402.

Dwyer W. O. et al., "Racial Differences In Color Vision: Do They Exist", American Journal of Optometry & Physiological Optics, 1975, 52, 224-229.

El Hage S.G., et al., "Contribution of the Crystalline Lens to the Spherical Aberration of the Eye," 1973, vol. 63 (2), pp. 205-211.

Futhey J.A., "Diffractive Bifocal Intraocular Lens," SPIE, 1989, vol. 1052, pp. 142-148.

Geun Y., et al., "Visual Performance after Correcting the Monchromatic and Chromatic Aberrations of the Eye," Journal of the Optical Society of America, 2002, vol. 19 (2), pp. 266-275.

Glasser A. et al., "Presbyopia and the optical changes in the human crystalline lens with age," Vision Res, 1998, 38 (2), 209-229.

Greivenkamp J.E., et al., "Visual Acuity Modeling Using Optical Raytracing Of Schematic Eyes," American Journal of Ophthalmology, 1995, vol. 120 (2), pp. 227-240.

Griswold Scott et al., "Scotopic Spectral Sensitivity of Phakic and Aphakic Observers Extending into the Near Ultraviolet," Vision res, 1992, 32 (9), 1739-1743.

Guirao A., et al., "Corneal Wave Aberration from Videokeratography: Accuracy And Limitations of the Procedure," Journal of the Optical Society of America, 2000, vol. 17 (6), pp. 955-965.

IOVS, 1999, 40 (4), S535.

Kiely et al., "The mean shape of the human cornea," Optica ACTA, 1982, 29 (8), 1027-1040.

(56) References Cited

OTHER PUBLICATIONS

Kokoschka S., et al., "Influence of Field Size on the Spectral Sensitivity of the Eye in the Photopic and Mesopic Range," American Journal of Optometry and Physiological Optics, 1985, vol. 62 (2), pp. 119-126.

Liang J., et al., "Objective Measurement Of Wave Aberrations Of The Human Eye With The Use Of A Hartmann-Shack Wave-Front Sensor," Journal of the Optical Society of America, 1994, vol. 11 (7), pp. 1949-1957.

Lindsay R., et al., "Descriptors of Corneal Shape," Optometry and Vision Science, 1998, vol. 75 (2), pp. 156-158.

Liou H.L., et al., "Anatomically Accurate, Finite Model Eye for Optical Modeling," Journal of Optical Society of America, Aug. 1997, vol. 14 (8), pp. 1684-1695.

Lotmar, "Theoretical eye model with aspherics," Journal of the Optical Society of America, 1971, 61 (11), 1522-1529.

Malacara D., et al., "Wavefront Fitting With Discrete Orthogonal Polynomials In a Unit Radius Circle," Optical Engineering, 1990, vol. 29 (6), pp. 672-675.

Mandell R.B., et al., "Mathematical Model of the Corneal Contour," 1965, School of Optometry, University of California, Berkeley, pp. 183-197.

Marcos S., et al., "A New Approach to the Study of Ocular Chromatic Aberrations," Vision Research, 1999, vol. 39 (26), pp. 4309-4323.

Marsack J.D., et al., "Metrics of Optical Quality Derived from Wave Aberrations Predict Visual Performance," Journal of Vision, Apr. 2004, vol. 4 (4), pp. 322-328.

Monsoriu J.A., et al., "Devil's Lenses," Optics Express, Oct. 17, 2007, vol. 15 (21), pp. 13858-13864.

Mordi J.A., et al., "Influence of Age of Chromatic Aberration of the Human Eye," American Journal of Optometry & Physiological Optics, 1985, vol. 62 (12), pp. 864-869.

Navarro R., et al., "Accommodation-Dependent Model of the Human Eye with Aspherics," Journal of the Optical Society of America, Aug. 1985, vol. 2 (8), pp. 1273-1281.

Norrby S., et al., "Model Eyes for Evaluation of Intraocular Lenses," Applied Optics, Sep. 7, 2007, vol. 46 (26), pp. 6595-6605.

"Optical Design," Military Standardization Handbook, 1962, Chapter 4, U.S. Department of Defense MIL-HDBK-141, 4-1-4-19.

Oshika T., et al., "Changes in Corneal Wavefront Aberrations with Aging," Investigative Ophthalmology & Visual Science, 1999, vol. 40 (7), pp. 1351-1355.

Patel S., et al., "Shape and Radius of Posterior Corneal Surface," Refractive and Corneal Surgery, 1993, vol. 9 (3), pp. 173-181.

Piers P.A.., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Said et al., "The Variation with Age of the Spectral Transmissivity of the Living Human Crystalline Lens," Gerontologia, 1959, 213-231.

Schwiegerling et al., "Representation of videokeratoscopic height data with Zernike polynomials," Journal of the Optical Society of America, 1995, 12 (10), 2105-2113.

Seitz B., et al., "Corneal Topography," Current Opinion in Ophthalmolgy, 1997, vol. 8 (4), pp. 8-24.

Siedlecki D., et al., "Radial Gradient index Intraocular Lens: a Theoretical Model," Journal of Modern Optics, Feb. 20-Mar. 10, 2008, vol. 55 (4-5), pp. 639-647.

Smith G., et al., "The Spherical Aberration of the Crystalline Lens of the Human Eye," Vision Res., 2001, vol. 41 (2), pp. 235-243.

Smith Kinney, "Sensitivity of the eye to spectral radiation at scotopic and mesopic intensity levels," Journal of the Optical Society of America, 1955, 45 (7), 507-514.

Sokołowski M., et al. "Hybrid Heptafocal Intraocular Lenses," Optica Applicata, Dec. 2015, vol. 45 (3), pp. 285-298.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Thibos L. N. et al., "The chromatic eye: a new reduced-eye model of ocular chromatic aberration in humans," Applied Optics, 1992, 31 (19), 3594-3600.

Thibos L. N. et al., "Theork and measurement of ocular chromatic aberration," Vision Res, 1988, 30 (1), 33-49.

Townsley, "New Knowledge of the corneal contour," Contacto, 1970, pp. 38-43.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Verriest G., "The Spectral Curve of Relative Luminous Efficiency in Different Age Groups of Aphakic Eyes," Mod Probl Ophthalmol., 1974, 13, 314-317.

Villegas E.A., et al., "Correlation between Optical and Psychophy, Sical Parameters as a Function of Defocus," Optometry and Vision Science, Jan. 1, 2002, vol. 79 (1), pp. 60-67.

Wang J.Y., et al., "Wave-Front Interpretation With Zernike Polynomials," Applied Optics, 1980, vol. 19 (9), pp. 1510-1518.

\* cited by examiner

ACHROMATIC LENSES AND LENSES HAVING DIFFRACTIVE PROFILES WITH IRREGULAR WIDTH FOR VISION TREATMENT

CROSS REFERENCE TO RELATED APPLICATIONS

The present application claims priority to U.S. Provisional Patent Application No. 62/955,355, filed on Dec. 30, 2019, the entire contents of which are incorporated by reference herein.

BACKGROUND

Embodiments of the present disclosure relate to vision treatment techniques and in particular, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only a limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL."

Monofocal IOLs are intended to provide vision correction at one distance only, usually the far focus. At the very least, since a monofocal IOL provides vision treatment at only one distance and since the typical correction is for far distance, spectacles are usually needed for good vision at near distances and sometimes for good vision at intermediate distances. The term "near vision" generally corresponds to vision provided when objects are at a distance from the subject eye at equal; or less than 1.5 feet. The term "distant vision" generally corresponds to vision provided when objects are at a distance of at least ab out 5-6 feet or greater. The term "intermediate vision" corresponds to vision provided when objects are at a distance of about 1.5 feet to about 5-6 feet from the subject eye. Such characterizations of near, intermediate, and far vision correspond to those addressed in Morlock R, Wirth R J, Tally S R, Garufis C, Heichel C W D, Patient-Reported Spectacle Independence Questionnaire (PRSIQ): Development and Validation. Am J Ophthalmology 2017; 178:101-114.

There have been various attempts to address limitations associated with monofocal IOLs. For example, multifocal IOLs have been proposed that deliver, in principle, two foci, one near and one far, optionally with some degree of intermediate focus. Such multifocal, or bifocal, IOLs are intended to provide good vision at two distances, and include both refractive and diffractive multifocal IOLs. In some instances, a multifocal IOL intended to correct vision at two distances may provide a near (add) power of about 3.0 or 4.0 diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these zones are typically annular lens zones, or echelettes, spaced aboutthe optical axis of the lens. Each echelette may be defined by an optical zone, a transition zone between the optical zone and an optical zone of an adjacent echelette, and an echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may also be in the form of a contact lens, most commonly a bifocal contact lens, or in any other form mentioned herein.

Although multifocal ophthalmic lenses lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area of improvement revolves around the typical bifocality of multifocal lenses. While multifocal ophthalmic lenses typically provide adequate near and far vision, intermediate vision may be compromised.

A lens with an extended range of vision may thus provide certain patients the benefits of good vision at a range of distances, while having reduced or no dysphotopsia. Various techniques for extending the depth of focus of an IOL have been proposed. One technique is embodied in the Tecnis Symfony® lens offered by Johnson& Johnson Vision. One technique may include a bulls-eye refractive principle, and may involve a central zone with a slightly increased power. One technique may include an asphere or include refractive zones with different refractive zonal powers.

Although certain proposed treatments may provide some benefit to patients in need thereof, further advances would be desirable. For example, it would be desirable to provide improved IOL systems and methods that confer enhanced image quality across a wide and extended range of foci without dysphotopsia. Embodiments of the present disclosure provide solutions that may address the problems described above, and hence may provide answers to at least some of these outstanding needs.

BRIEF SUMMARY

Embodiments herein described include ophthalmic lenses including an optic. The optic may include a diffractive profile including at least one set of echelettes, each echelette of the set having a different width in r-squared space than any other echelette of the set and the at least one set of echelettes repeating at least once upon the optic.

Embodiments herein described include a method comprising fabricating an optic for an ophthalmic lens, the optic including a diffractive profile including at least one set of echelettes, each echelette of the set having a different width in r-squared space than any other echelette of the set and the at least one set of echelettes repeating at least once upon the optic.

Embodiments herein described include a system for fabricating an ophthalmic lens. The system may include a processor configured to determine a diffractive profile of an optic, the diffractive profile including at least one set of echelettes, each echelette of the set having a different width in r-squared space than any other echelette of the set and the at least one set of echelettes repeating at least once upon the optic. The system may include a manufacturing assembly that fabricates the optic based on the diffractive profile.

Embodiments herein described include ophthalmic lenses including an optic. The optic may include a diffractive profile including a plurality of echelettes, at least one echelette of the diffractive profile having a same width in r-squared space as another echelette of the diffractive profile, and at least one echelette of the diffractive profile having a different width in r-squared space than any other echelette of the diffractive profile.

Embodiments herein described include a method comprising fabricating an optic for an ophthalmic lens, the optic including a diffractive profile including a plurality of echelettes, at least one echelette of the diffractive profile having a same width in r-squared space as another echelette of the diffractive profile, and at least one echelette of the diffractive profile having a different width in r-squared space than any other echelette of the diffractive profile.

Embodiments herein described include a system for fabricating an ophthalmic lens. The system may include a processor configured to determine a diffractive profile of an optic, the diffractive profile including a plurality of echelettes, at least one echelette of the diffractive profile having a same width in r-squared space as another echelette of the diffractive profile, and at least one echelette of the diffractive profile having a different width in r-squared space than any other echelette of the diffractive profile. The system may include a manufacturing assembly that fabricates the optic based on the diffractive profile.

Embodiments herein described include ophthalmic lenses including an optic. The optic may include a diffractive profile including at least one echelette having a power and having a different width in r-squared space than another echelette of the diffractive profile, the at least one echelette being configured to distribute light to a distance focus.

The optic may include a refractive profile having a refractive zone with a width corresponding to the width of the at least one echelette and having a power that is negative or positive with respect to the power of the at least one echelette, the refractive zone configured to vary the distance focus of the at least one echelette.

Embodiments herein described include a method comprising fabricating an optic for an ophthalmic lens. The optic may include a diffractive profile including at least one echelette having a power and having a different width in r-squared space than another echelette of the diffractive profile, the at least one echelette being configured to distribute light to a distance focus.

The optic may include a refractive profile having a refractive zone with a width corresponding to the width of the at least one echelette and having a power that is negative or positive with respect to the power of the at least one echelette, the refractive zone configured to vary the distance focus of the at least one echelette.

Embodiments herein described include a system for fabricating an ophthalmic lens. The system may include a processor configured to determine a diffractive profile and a refractive profile of an optic, the diffractive profile including at least one echelette having a power and having a different width in r-squared space than another echelette of the diffractive profile, the at least one echelette being configured to distribute light to a distance focus, and the refractive profile having a refractive zone with a width corresponding to the width of the at least one echelette and having a power that is negative or positive with respect to the power of the at least one echelette, the refractive zone configured to vary the distance focus of the at least one echelette.

The system may include a manufacturing assembly that fabricates the optic based on the diffractive profile and the refractive profile.

Embodiments herein described include ophthalmic lenses including an optic. The optic including a diffractive profile including a plurality of echelettes, each echelette of the diffractive profile having a different width in r-squared space than any other echelette of the diffractive profile.

Embodiments herein described include a method comprising fabricating an optic for an ophthalmic lens, the optic including a diffractive profile including a plurality of echelettes, each echelette of the diffractive profile having a different width in r-squared space than any other echelette of the diffractive profile.

Embodiments herein described include a system for fabricating an ophthalmic lens. The system may include a processor configured to determine a diffractive profile of an optic, the diffractive profile including a plurality of echelettes, each echelette of the diffractive profile having a different width in r-squared space than any other echelette of the diffractive profile. The system may include a manufacturing assembly that fabricates the optic based on the diffractive profile.

DETAILED DESCRIPTION

FIGS. 1A, 1B, 2A, 2B, 3A and 3B illustrate multifocal IOL lens geometries, aspects of which are described in U.S. Patent Publication No. 2011-0149236 A1, which is hereby incorporated by reference in its entirety.

Figure 1A:
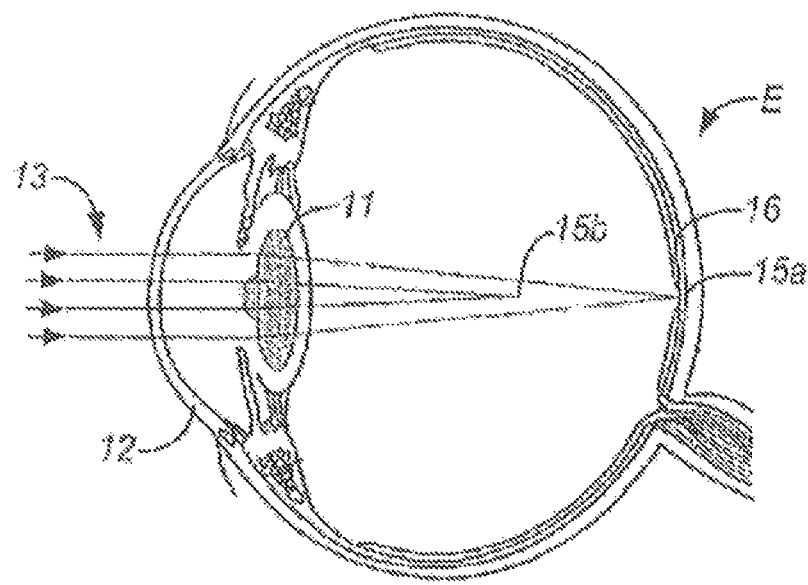
FIG. 1A illustrates a cross-sectional view of an eye with an implanted multifocal refractive intraocular lens.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens. One or more support elements may be configured to secure the lens 11 to a patient's eye.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
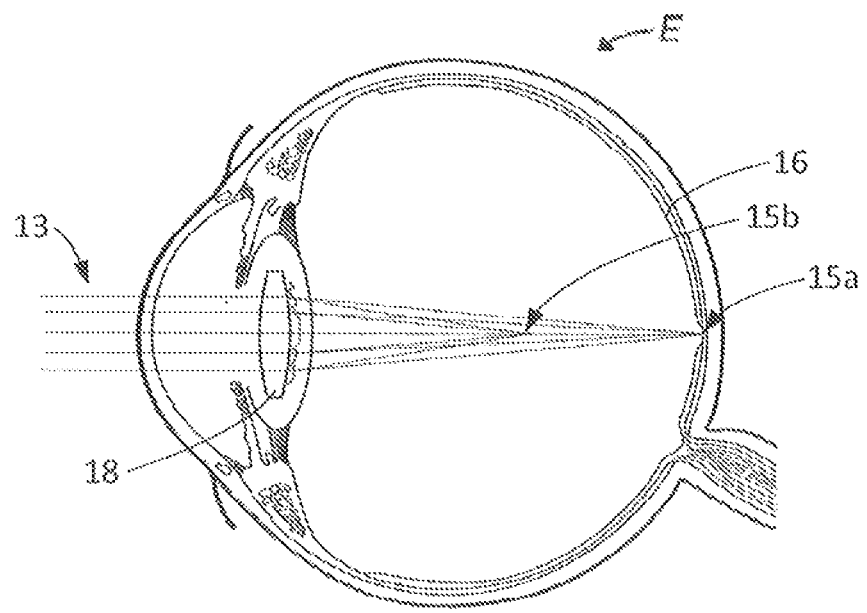
FIG. 1B illustrates a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative power, and that diffractive power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light 13 enters from the front of the eye, the multifocal lens 18 directs light 13 to form a far field focus 15a on retina 16 for viewing distant objects and a near field focus 15b for viewing objects close to the eye. Depending on the distance from the source of light 13, the focus on retina 16 may be the near field focus 15b instead. Typically, far field focus 15a is associated with $0^{th}$ diffractive order and near field focus 15b is associated with the $1^{st}$ diffractive order, although other orders may be used as well.

Bifocal ophthalmic lens 18 typically distributes the majority of light energy into two viewing orders, often with the goal of splitting imaging light energy about evenly (50%: 50%), one viewing order corresponding to far vision and one viewing order corresponding to near vision, although typically, some fraction goes to non-viewing orders.

Corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present disclosure may be applied to inlays, onlays, accommodating IOLs, pseudophakic IOLs, other forms of intraocular implants, spectacles, and even laser vision correction.

Figure 2A:
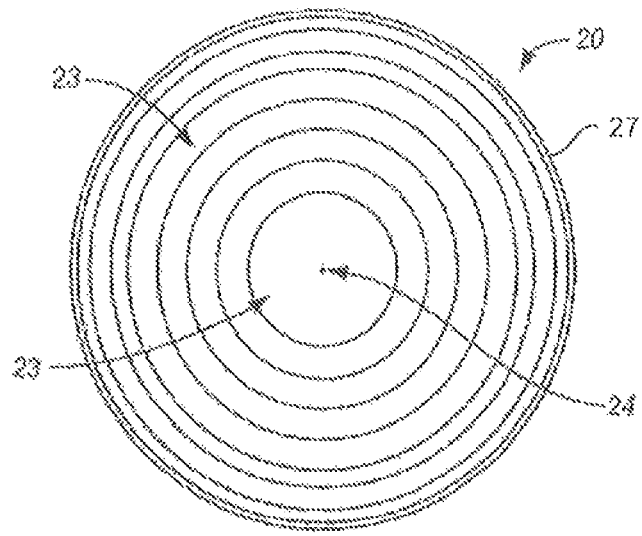
FIG. 2A illustrates a front view of a diffractive multifocal intraocular lens.
Figure 2B:
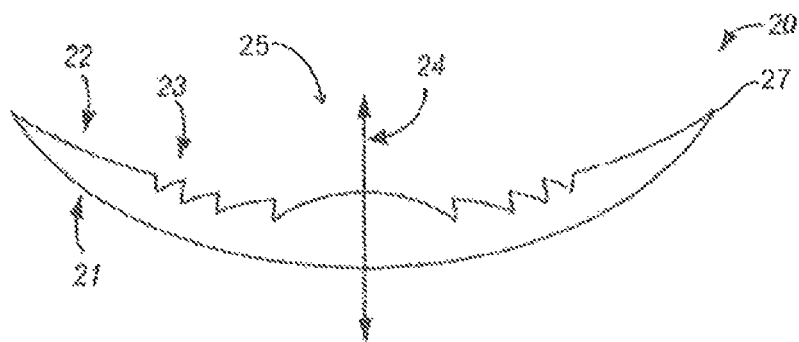
FIG. 2B illustrates a cross-sectional view of a diffractive multifocal intraocular lens.

FIGS. 2A and 2B show aspects of a conventional diffractive multifocal lens 20. Multifocal lens 20 may have certain optical properties that are generally similar to those of multifocal IOLs 11, 18 described above. Multifocal lens 20 has an anterior lens face 21 and a posterior lens face 22 disposed about an optical axis 24 that is at the central zone 25 of the lens 20. The faces 21, 22, or optical surfaces, extend radially outward from the optical axis 24 to an outer periphery 27 of the optic. The faces 21, 22, or optical surfaces, face opposite each other.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular diffractive zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Figure 3A:
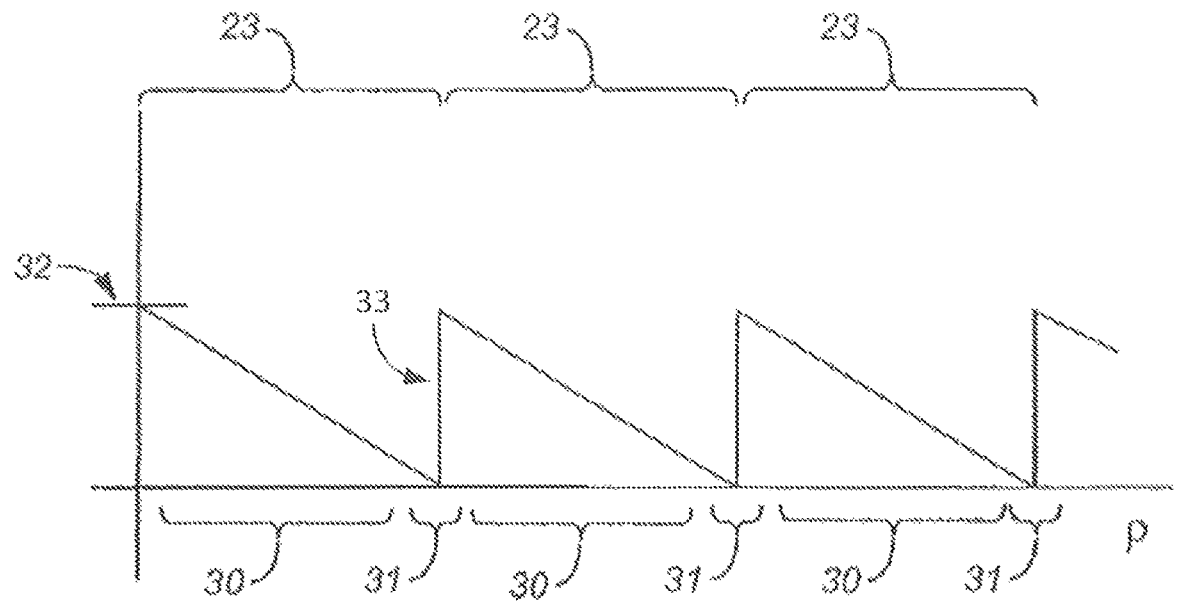
FIGS. 3A-3B are graphical representations of a portion of the diffractive profile of a conventional diffractive multifocal lens.
Figure 3B:
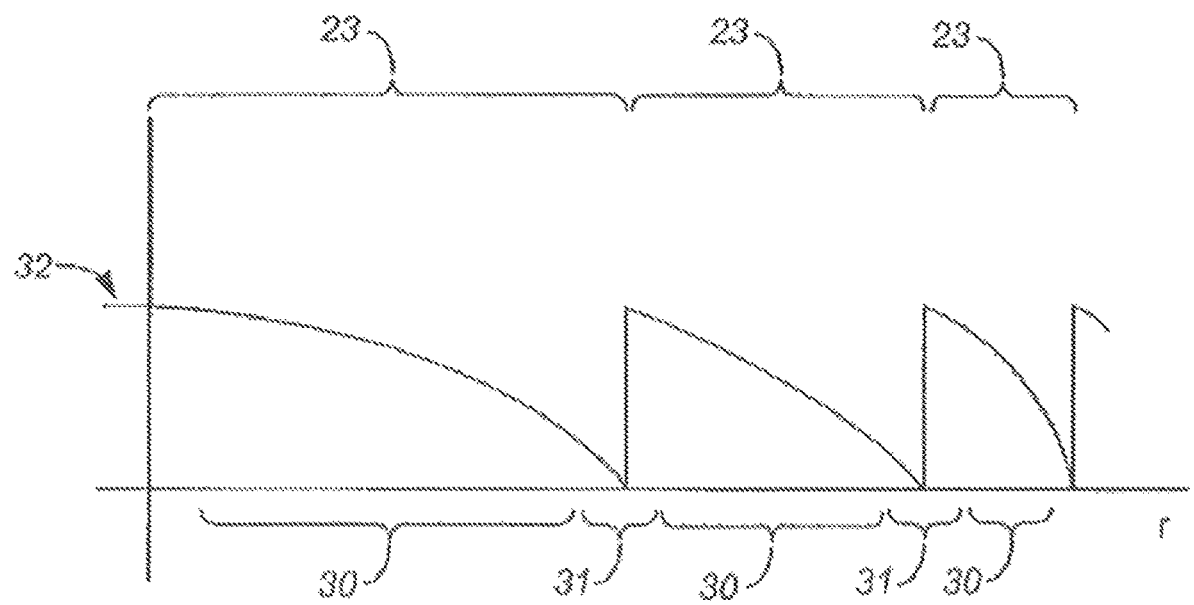

FIGS. 3A and 3B are graphical representations of a portion of a typical diffractive profile of a multifocal lens. While the graph shows only 3 echelettes, typical diffractive lenses extend to at least 9 echelettes to over 32 echelettes. In FIG. 3A, the height 32 of the surface relief profile (from a plane perpendicular to the light rays) of each point on the echelette surface is plotted against the square of the radial distance ($r^2$ or $\rho$) from the optical axis of the lens (referred to as r-squared space). In multifocal lenses, each echelette 23 may have a diameter or distance from the optical axis which is often proportional to $\sqrt{n}$, n being the number of the echelette 23 as counted from the optical axis 24. Each echelette has a characteristic optical zone 30 and transition zone 31. Optical zone 30 typically has a shape or downward slope that is parabolic as shown in FIG. 3B. The slope of each echelette in r-squared space (shown in FIG. 3A), however, is the same. As for the typical diffractive multifocal lens, as shown here, all echelettes have the same surface area. The area of echelettes 23 determines the diffractive power of lens 20, and, as area and radii are correlated, the diffractive power is also related to the radii of the echelettes. The physical offset of the trailing edge of each echelette to the leading edge of the adjacent echelette is the step height. An exemplary step height between adjacent echelettes is marked as reference number 33 in FIG. 3A. The step heights remain the same in r-squared space (FIG. 3A) and in linear space (FIG. 3B). The step offset is the height offset of the transition zone from the underlying base curve. An exemplary step offset is marked as reference number 501 in FIG. 5.

Figure 4:
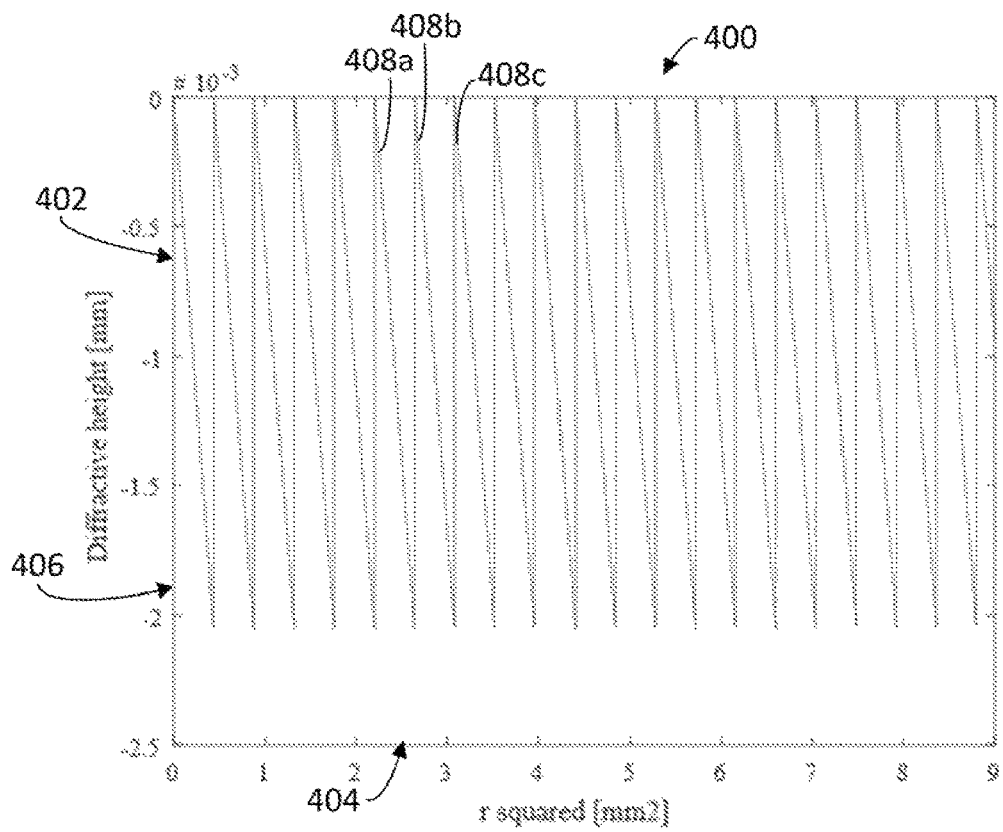
FIG. 4 illustrates a diffractive profile of a bifocal optic.

Conventional multifocal diffractive lenses typically provide for near and far vision, neglecting visual performance at intermediate distances. FIG. 4, for example, illustrates a diffractive profile of a bifocal optic. The diffractive profile 400 is shown relative to the Y axis 402, which represents the phase shift of the diffractive profile 400. The height is shown in units of millimeter (mm), and may represent the distance from the base spherical wavefront generated by the lens. In other embodiments, other units or scalings may be utilized. The height or phase shift of the diffractive profile 400 is shown in relation to the radius on the X axis 404 from the optical axis 406 in r-squared space. The radial coordinate represents the distance from the optical axis 406 in r-squared space, and is shown in units of millimeters squared, although in other embodiments, other units or scalings may be utilized.

The diffractive profile 400 includes a plurality of echelettes (representative echelettes 408a, 408b, 408c are marked) that each have the same width in r-squared space. The step height of each echelette is also the same in the diffractive profile 400. The diffractive pattern accordingly may direct light to two focuses (forming a bifocal optic).

Figure 5:
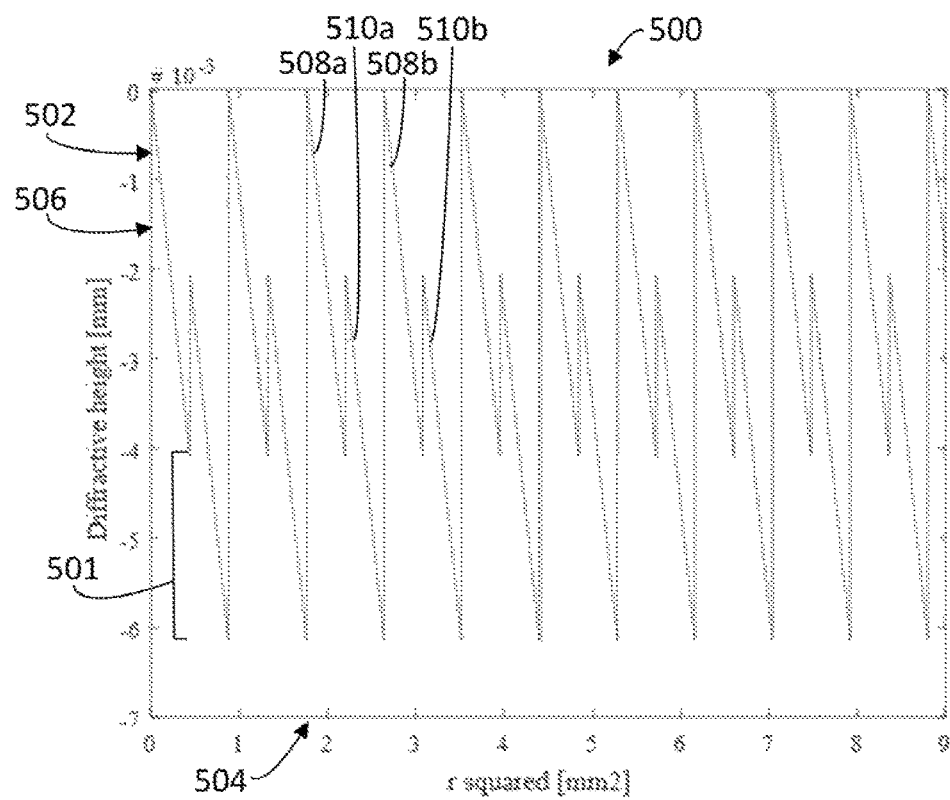
FIG. 5 illustrates a diffractive profile of a trifocal optic.

FIG. 5 illustrates a diffractive profile of a trifocal optic. The diffractive profile 500 is shown relative to the Y axis 502, which represents the phase shift of the diffractive profile 500. The height is shown in units of millimeter (mm), and may represent the distance from the base spherical wavefront generated by the lens. In other embodiments, other units or scalings may be utilized. The height or phase shift of the diffractive profile 500 is shown in relation to the radius on the X axis 504 from the optical axis 506 in r-squared space. The radial coordinate represents the distance from the optical axis 506 in r-squared space, and is shown in units of millimeters squared, although in other embodiments, other units or scalings may be utilized.

The diffractive profile 500 includes a plurality of echelettes. The echelettes are provided as repeating set of two different echelettes, with one configuration of echelette being marked in FIG. 5 as echelettes 508a, 508b, and another configuration of echelette being marked in FIG. 5 as echelette 510a, 510b. The width in r-squared space and the step height and step offset of each configuration of echelette (e.g., echelette 508a, 508b) is repeated upon the optic. The echelettes 508a, 508b for example have the same width in r-squared space as each other, and the echelettes 510a, 510b have the same width in r-squared space as each other. The diffractive pattern accordingly may direct light to three focuses (forming a trifocal optic).

Figure 6:
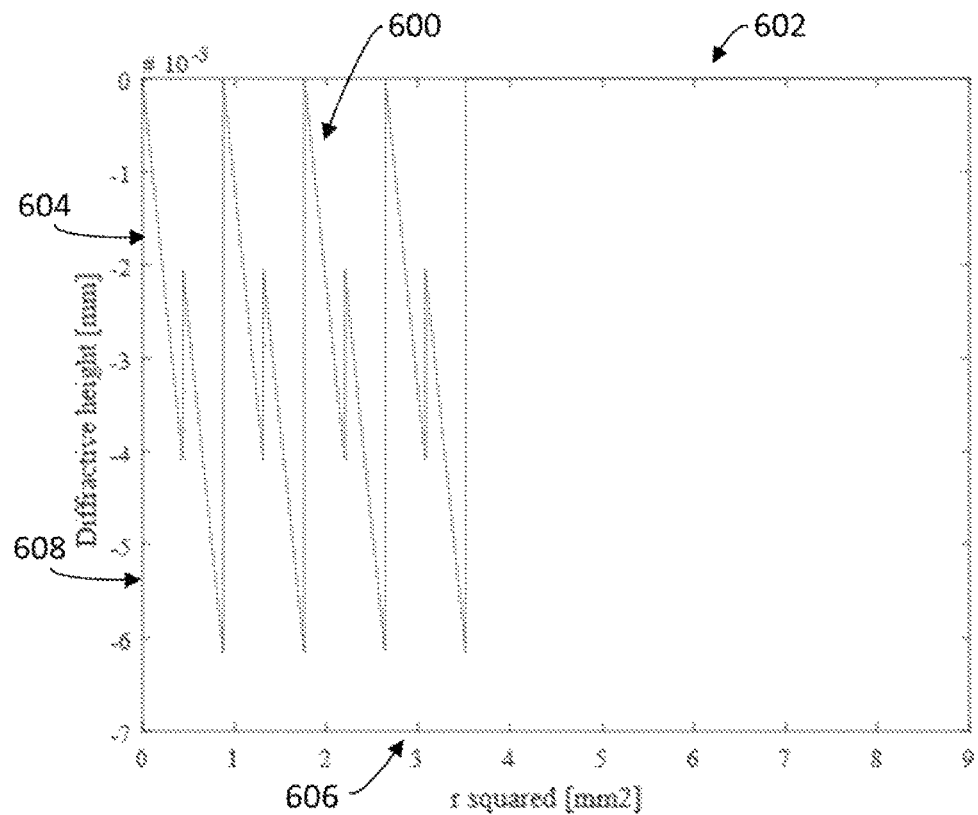
FIG. 6 illustrates a profile of an optic in which a trifocal diffractive pattern is only positioned on a central zone of an optic, with a peripheral zone including a refractive surface.

The optic represented in FIG. 5 may be modified to include at least one zone that does not include the diffractive pattern. FIG. 6 for example represents an optic in which a trifocal diffractive pattern 600 is only positioned on a central zone of an optic, with a peripheral zone including a refractive surface 602. In FIG. 6, the diffractive profile 600 is shown relative to the Y axis 604, which represents the phase shift of the diffractive profile 600. The height is shown in units of millimeters (mm), and may represent the distance from the base spherical wavefront generated by the lens. In other embodiments, other units or scalings may be utilized. The height or phase shift of the diffractive profile 600 is shown in relation to the radius on the X axis 606 from the optical axis 608 in r-squared space. The radial coordinate represents the distance from the optical axis 608 in r-squared space, and is shown in units of millimeters squared, although in other embodiments, other units or scalings may be utilized.

Figure 7:
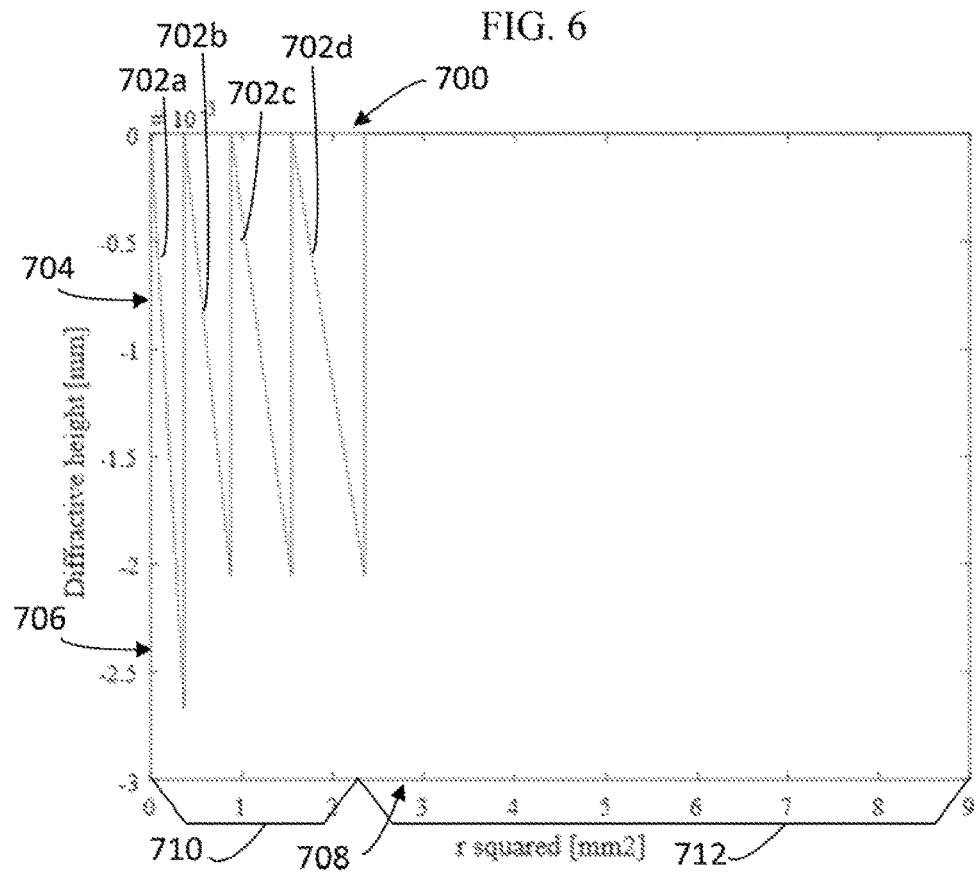
FIG. 7 illustrates a profile of an optic that does not include echelettes that repeat having the same width in r-squared space.

FIG. 7 illustrates an embodiment of an optic that does not include echelettes that repeat having the same width in r-squared space. The optic includes a diffractive profile 700 including a plurality of echelettes, each echelette of the diffractive profile 700 having a different width in r-squared space than any other echelette of the diffractive profile 700. In embodiments, each echelette of the diffractive profile 700 may be configured to distribute light to a distance focus. The diffractive profile 700 may serve to provide for an extended range of vision that may help to improve the visual performance at intermediate distances and may reduce other visual symptoms associated with diffractive optics including glare and halos.

In the embodiment of FIG. 7, a diffractive profile 700 is provided that includes a plurality of echelettes 702a-d and that is disposed on a surface of an optic such that each one of the plurality of echelettes 702a-d have a different width than each other in r-squared space. The diffractive profile 700 is shown relative to the Y axis 706, which represents the phase shift of the diffractive profile 700. The height is shown in units of millimeter (mm), and may represent the distance from the base spherical wavefront generated by the lens. In other embodiments, other units or scalings may be utilized. The height or phase shift of the diffractive profile 700 is shown in relation to the radius on the X axis 708 from the optical axis 704 in r-squared space. The radial coordinate represents the distance from the optical axis 704 in r-squared space, and is shown in units of millimeters squared, although in other embodiments, other units or scalings may be utilized.

Each echelette 702a-d may be positioned on a surface of the optic, with the surface extending radially outward from the optical axis 704 to the outer periphery of the optic (such as the outer periphery 27 marked in FIG. 2B). Each echelette 702a-d may be positioned adjacent to each other, as shown in FIG. 7, or in other embodiments spacings may be provided between the echelettes 702a-d.

The different widths in r-squared space of the echelettes 702a-d may correspond to different diffractive or add powers of the optic. The echelette 702b for example, may correspond to a diffractive or add power of 3 diopter, for example. The echelette 702c for example, may correspond to a diffractive or add power of 2.4 diopter, for example. The echelette 702d for example, may correspond to a diffractive or add power of 1.8 diopter, for example. The corresponding diffractive or add power may be different for each echelette 702a-d. Various other diffractive or add powers may be utilized as desired.

In embodiments, the echelettes 702a-d may each distribute some light to a distance focus, to provide a smooth, extended depth of focus or extended range of vision for the individual, decreased visual symptoms, and improved distance vision. Further, at least one of the echelettes 702a-d may be configured to distribute light to a near focus or to an intermediate focus. In embodiments, the echelettes 702a-d may be configured to split light to both a distance focus and a near focus, or to a distance focus, an intermediate focus, and/or a near focus.

The irregular width of the echelettes 702a-d may provide a smooth, extended depth of focus or extended range of vision for the individual and may break the symmetry between the r-squared distances of transition zones between the echelettes, thus reducing undesired visual symptoms. The diffractive profile may form an extended depth of focus. The diffractive profile may also modify chromatic aberration in a distance focus. Combinations of features may be provided as desired.

One or more of the echelettes 702a-d may have the same step height as each other. For example, as shown in FIG. 7, the echelettes 702b-d may have the same step heights as each other. In other embodiments, any or at least two of the echelettes 702a-d may have a same step height or a different step height than each other.

In one embodiment, the diffractive profile 700 may include a plurality of echelettes 702a-d disposed on a surface of the optic such that each one of the plurality of echelettes 702a-d between the optical axis and the outer periphery of the optic has a different width in r-squared space than any other echelette on the surface of the optic between the optical axis and the outer periphery of the optic.

In one embodiment, the echelettes 702a-d of the diffractive profile 700 may be positioned in a central zone 710, that the optical axis 704 may pass through. The optic may include a peripheral zone 712 positioned radially outward of the central zone 710, which may not include a diffractive profile in certain embodiments. The peripheral zone 712 as shown in FIG. 7 may include a refractive surface, which may be adjacent to the central zone 710 and the diffractive profile 700. Other configurations of optic may be utilized, for example, the diffractive profile 700 may extend outward to the outer periphery of the optic in certain embodiments, or a central zone 710 may not include a diffractive profile, with a peripheral zone including a diffractive profile, or an intermediate zone (between refractive surfaces) including a diffractive profile. In embodiments, the central zone 710 may include a refractive surface that may be positioned radially inward of the diffractive profile 700. In embodiments, a refractive surface may provide one or more of an intermediate focus, a near focus, or an extended depth of focus.

The number of echelettes of the diffractive profile 700 may vary. For example, the number may include two echelettes. The number may include at least three echelettes. The number may include at least four echelettes. The number may include at least five echelettes. A greater or lesser number of echelettes may be utilized as desired. In each embodiment, a step height of at least two of the echelettes may be the same, or a step height of at least two of the echelettes may be different.

Figure 8:
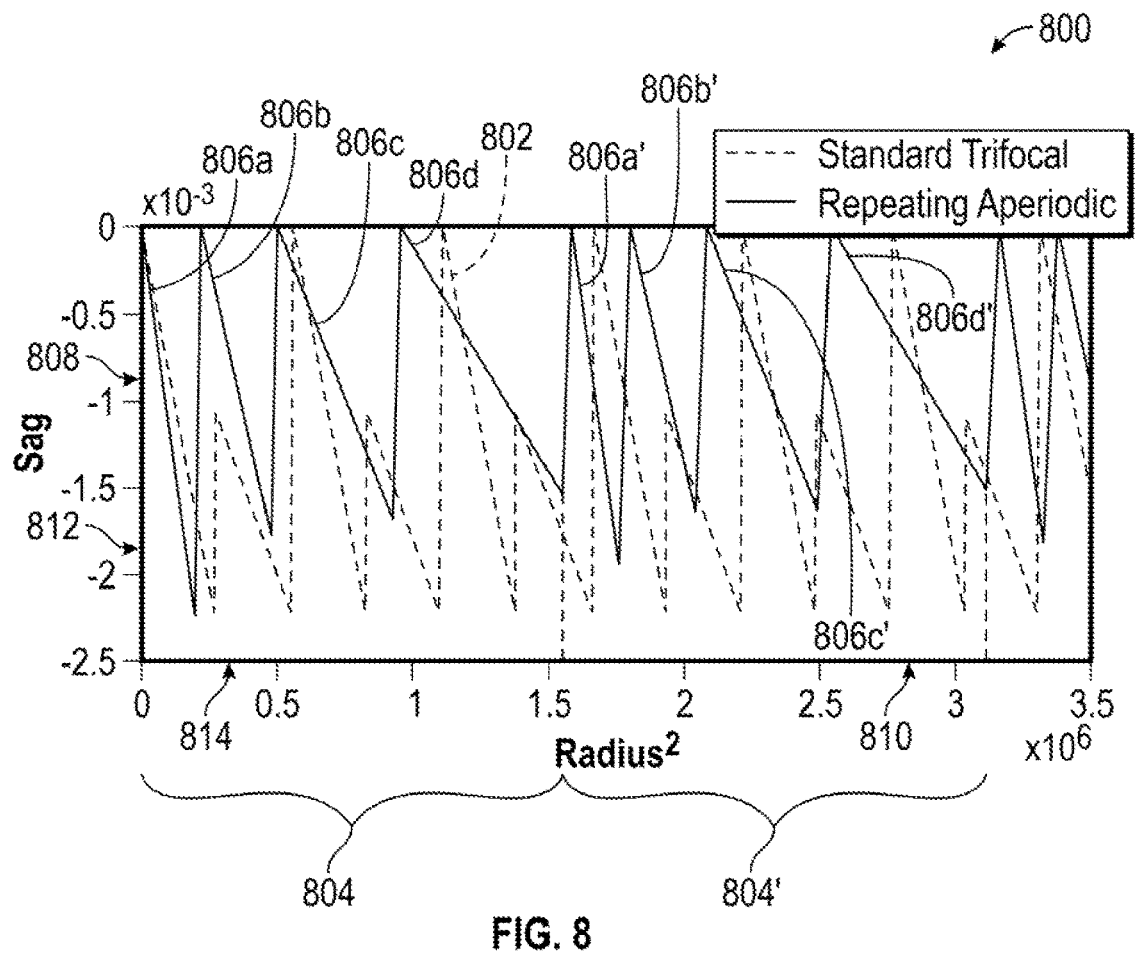
FIG. 8 illustrates a profile of an optic including a set of echelettes that repeat.

In embodiments, a diffractive profile may include at least one set of echelettes, with each echelette of the set having a different width in r-squared space than any other echelette of the set. In embodiments, the at least one set may repeat at least once upon the optic. FIG. 8, for example, illustrates an embodiment in solid lines of a diffractive profile 800 of such an embodiment. FIG. 8 illustrates in dashed lines a profile 802 of a trifocal optic, such as shown in FIG. 5, for comparison purposes with the diffractive profile 800 shown in solid lines.

The diffractive profile 800 includes at least one set 804 of echelettes 806a-d. The echelettes 806a-d of the set 804 each have a different width in r-squared space than any other echelette of the set 804. The set 804 includes four echelettes 806a-d, however, in embodiments, the set may include a greater or lesser number of echelettes. For example, the set 804 may include two echelettes, three echelettes, four echelettes, five echelettes, or may include at least two, at least three, at least four, at least five echelettes, etc. as desired.

The echelettes 806a-d of the set 804 are shown relative to the Y axis 808, which represents the phase shift of the diffractive profile 800. The height or phase shift of the diffractive profile 800 is shown in relation to the radius on the X axis 810 from the optical axis 812 in r-squared space. The radial coordinate represents the distance from the optical axis 812 in r-squared space, and is shown in units of millimeters squared, although in other embodiments, other units or scalings may be utilized.

Each echelette 806a-d may be positioned on a surface of the optic, with the surface extending radially outward from the optical axis 812 to the outer periphery of the optic (such as the outer periphery 27 marked in FIG. 2B). Each echelette 806a-d may be positioned adjacent to each other, as shown in FIG. 8, or in other embodiments spacings may be provided between the echelette 806a-d.

Each echelette 806a-d of the set 804 may have a different step height and step offset as shown in FIG. 8, or in embodiments any number may have the same step height or step offset as desired. For example, at least two echelettes 806a-d of the set may have a same step height and/or step offset, or at least two echelettes 806a-d of the set may have a different step height and/or step offset.

The set 804 may be positioned at a central zone 814 of the optic, or may be positioned at a different location as desired. For example, in embodiments, the set 804 may be at a distance from the optical axis 812 and may be in an intermediate zone or peripheral zone of the optic in embodiments. In embodiments, a peripheral zone may be provided that may include a refractive surface. In embodiments, the central zone 814 may include a refractive surface that is positioned radially inward of the diffractive profile. The optic may include a refractive surface that may provide one or more of an intermediate focus, a near focus, or an extended depth of focus.

The set 804 may repeat upon the optic at least once. In the embodiment shown in FIG. 8, for example, the set 804 is repeated upon the optic to form repeated set 804' including the repeated echelettes 806a', 806b', 806c', and 806d'. The repeated set 804' is shown adjacent to the set 804, although in embodiments a spacing or other portion of the diffractive profile may be positioned between the sets 804, 804'. The echelettes 806*a*′, 806*b*′, 806*c*′, and 806*d*′ of the repeated set 804′ may be identical to the respective echelettes 806*a*, 806*b*, 806*c*, and 806*d* of the original set 804, and may have the same width in r-squared space as the respective original echelette 806*a*, 806*b*, 806*c*, and 806*d* of the original set 804.

In embodiments, the set 804 may repeat more than once upon the optic. For example, the set 804 may repeat twice upon the optic, or at least twice upon the optic in embodiments (e.g, three times, four times, etc.). The set 804 may repeat at least three times upon the optic, or at least four times, etc. In embodiments, the set 804 may repeat along an entire pupillary zone of the optic, comprisingthe portion of the optic exposed to light through the patient's pupil. The pupillary zone may extend outward from the optical axis 812 towards the outer periphery of the optic. The set 804 may be repeated a desired number of times to cover the entire pupillary zone in embodiments as desired. In other embodiments, only a portion of the optic or the pupillary zone may include a repeating set of echelettes.

The optic may include a single repeating set of echelettes, or may include multiple different sets of echelettes that repeat. In embodiments, each echelette of the respective set may have a different width in r-squared space than any other echelette of that set. In embodiments, the set may not repeat upon the optic. For example, FIG. 7 illustrates an embodiment of a set 702*a*, 702*b*, 702*c*, 702*d* that does not repeat upon the optic.

In an embodiment as shown in FIG. 8, each echelette, or at least one echelette of the set, may be configured to distribute light to a near focus or may be configured to distribute light to an intermediate focus. The diffractive profile 800 may form an extended depth of focus. The diffractive profile may also modify chromatic aberration in a distance focus. Combinations of features may be provided as desired.

Figure 9:
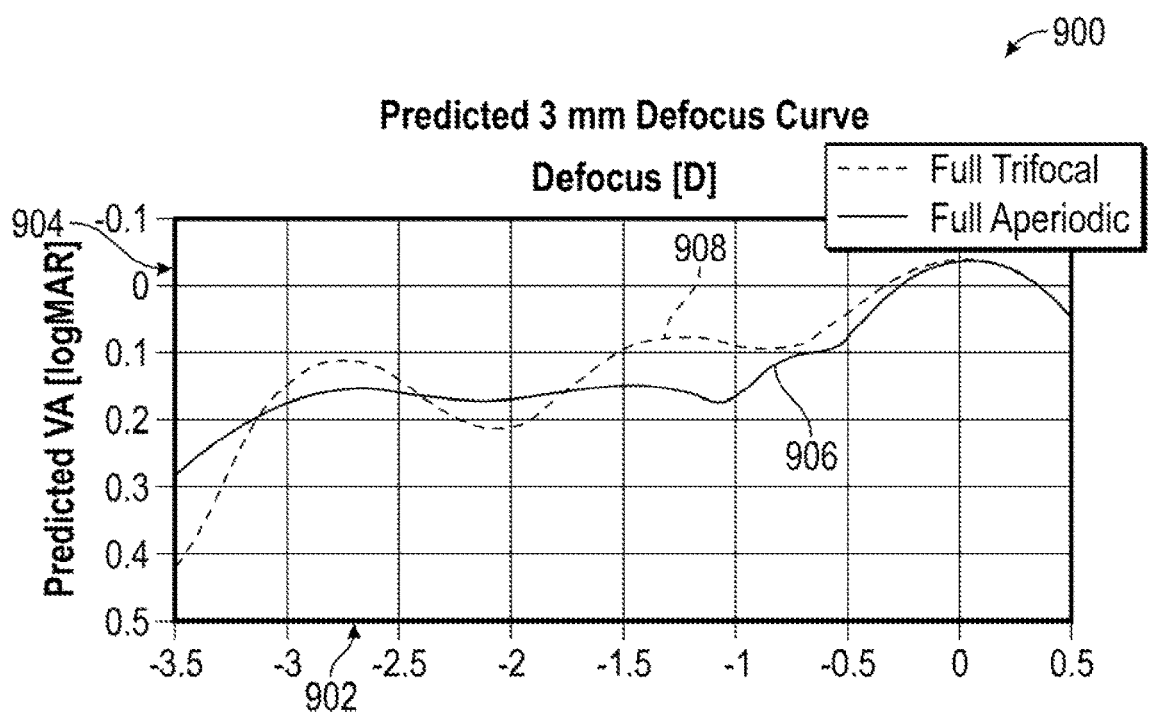
FIG. 9 illustrates a graph of a predicted defocus curve for the profile of the optic shown in FIG. 8.

The repeating set of echelettes, as shown in FIG. 8, may be repeated throughout the whole pupil to provide improved distance and near vision, and a continuous range of vision for a variety of pupil sizes including large pupil sizes. FIG. 9, for example, illustrates a graph 900 of defocus for the diffractive profile 800 shown in FIG. 8, with defocus in units of diopter shown on the X-axis 902 and predicted visual acuity shown on the Y-axis 904. The defocus 906 of the diffractive profile 800 shown in FIG. 8 for a 3 millimeter pupil is shown in solid line, with the defocus 908 of a trifocal diffractive profile (as shown in FIG. 8 in dashed lines) shown for comparison. The defocus 906 of the diffractive profile is shown to provide an improved continuous range of vision, whereas the trifocal diffractive profile is shown to have three distinct peaks.

In embodiments, a diffractive profile may result in correction of chromatic aberration. A diffractive profile may inherently compensate partially or fully for a longitudinal chromatic aberration of the eye. Correction of chromatic aberration may occur by having a diffractive profile with a step size of 1 wavelength or higher. This may occur in monofocal, multifocal, or extended depth of focus lenses.

An aperiodic diffractive profile, as shown in FIGS. 7 and 8 for example, may result in correction of longitudinal chromatic aberration, yet may direct light to different distance foci. An echelette of an aperiodic diffractive profile having a corresponding diffractive power of 2.5 diopter, for example may direct light to a different distances than an echelette of the profile having a corresponding diffractive power of 1.5 diopter.

In embodiments, a diffractive profile may be provided that may include a plurality of echelettes, with at least one echelette of the diffractive profile having a same width in r-squared space as another echelette of the diffractive profile, and at least one echelette of the diffractive profile having a different width in r-squared space than any other echelette of the diffractive profile.

Figure 10:
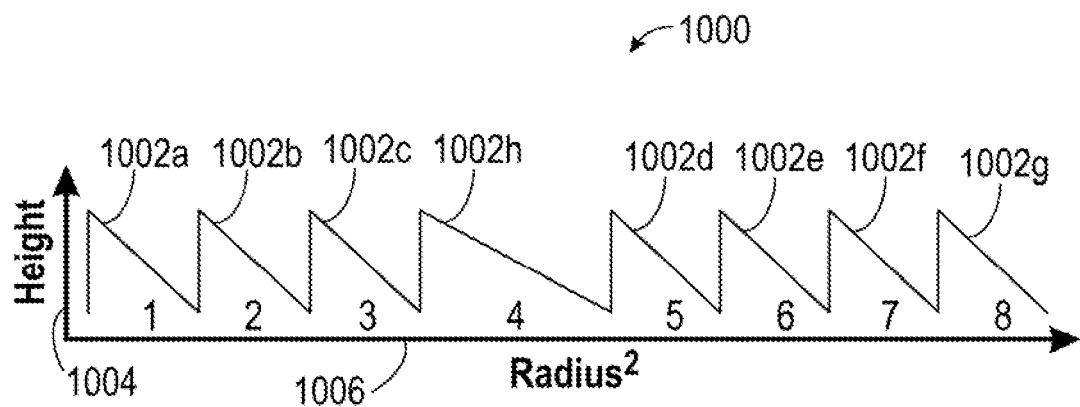
FIG. 10 illustrates a profile of an optic in which at least one echelette of the diffractive profile has a different width in r-squared space than any other echelette of the diffractive profile.

FIG. 10, for example, illustrates such an embodiment, in which a diffractive profile 1000 is provided, with at least one echelette 1002*a* having a same width in r-squared as another echelette 1002*b* of the diffractive profile 1000, and at least one echelette 1002*h* of the diffractive profile 1000 having a different width in r-squared space than any other echelette of the diffractive profile 1000. The echelettes 1002*a*-*h* of the profile 1000 are shown relative to the Y axis 1004, which represents the phase shift of the diffractive profile 1000. The height or phase shift of the diffractive profile 1000 is shown in relation to the radius on the X axis 1006 from an optical axis in r-squared space.

The echelette 1002*a* has a same width in r-squared space than other echelettes 1002*b*, *c*, *d*-*g* of the profile 1000, yet has a different width than the echelette 1002*h*. Thus, in embodiments, at least one echelette 1002*h* may have a different width in r-squared space than any other echelette of the profile 1000, with the remaining echelettes 1002*a*-*c*, *d*-*g* each having the same with in r-squared space. Various other modifications may be provided (e.g., at least two echelettes may have a different width in r-squared space than any other echelette of the diffractive profile, at least three, at least four, etc.). Further, the number of echelettes that have a same width in r-squared space may be varied in embodiments as desired, for example, two echelettes of the diffractive profile may have a same width in r-squared space as each other, at least three, at least four, etc.

The total number of echelettes of the diffractive profile 1000 may be varied as desired. For example, in embodiments, the plurality of echelettes of the diffractive profile 1000 may include at least three echelettes, at least four echelettes, at least five echelettes, etc. Eight echelettes are shown as marked in FIG. 10, however a greater or lesser number of echelettes may be provided in FIG. 10, and in all other embodiments of diffractive profiles disclosed herein. The echelettes of the diffractive profile 1000 may each have a same step height as each other or a different step height. In embodiments, at least two of the echelettes of the diffractive profile may have a different step height. In embodiments, at least two of the echelettes of the diffractive profile may have a same step height. Various modifications may be provided as desired.

Features of other embodiments disclosed herein may be utilized with the diffractive profile. For example, at least one echelette of the diffractive profile may be configured to distribute light to a distance focus. In embodiments, at least one echelette of the diffractive profile may be configured to distribute light to a near focus or to an intermediate focus. The diffractive profile may form an extended depth of focus. The diffractive profile may also modify chromatic aberration in a distance focus. Combinations of features may be provided as desired.

Other features may be utilized with the diffractive profile. For example, the diffractive profile 1000 may be disposed on a first surface of an optic such that at least one echelette of the diffractive profile on the first surface between the optical axis and the outer periphery of the optic has a same width in r-squared space as another echelette of the diffractive profile on the first surface between the optical axis and the outer periphery of the optic. At least one echelette of the diffractive profile on the first surface between the optical axis and the outer periphery of the optic may have a different width in r-squared space than any other echelette of the diffractive profile on the first surface between the optical axis and the outer periphery of the optic. The optic may include a central zone and a peripheral zone, and the diffractive profile may be positioned on the central zone, and the peripheral zone may include a refractive surface. A refractive surface as disclosed herein may provide one or more of an intermediate focus, a near focus, or an extended depth of focus.

In embodiments, a central zone may include a refractive surface that is positioned radially inward of the diffractive profile 1000. Various other modifications and combinations of features across embodiments may be provided as desired.

Figure 11:
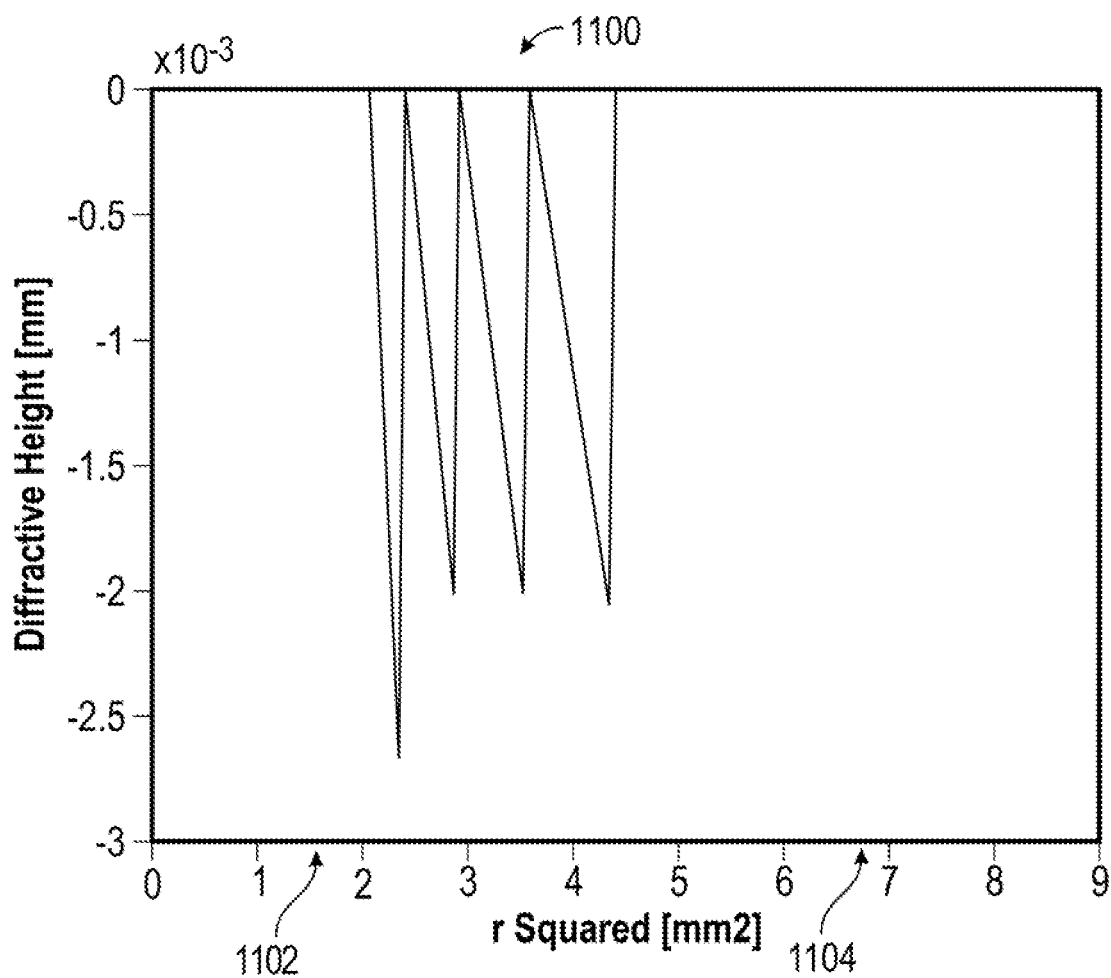
FIG. 11 illustrates a profile of an optic including a central zone including a refractive profile and a diffractive profile, and a peripheral zone including a refractive surface.

FIG. 11, for example, illustrates an embodiment of a diffractive profile 1100 configured similarly as the profile shown in FIG. 7, yet with a central zone 1102 including a refractive surface. The refractive surface of the central zone 1102 is positioned radially inward of the diffractive profile 1100. The profile further includes a refractive surface positioned in a peripheral zone 1104. The central zone 1102 includes the diffractive profile 1100, which may be intermediate of the refractive surfaces of the central zone 1102 and the peripheral zone 1104. The diffractive profile 1100 may be adjacent to the refractive surface of the central zone 1102 and the refractive surface of the peripheral zone 1104. Any embodiment of diffractive profile disclosed herein may include a central zone having a refractive surface positioned radially inward of the diffractive profile.

In embodiments, to receive benefits of correction of longitudinal chromatic aberration provided by an aperiodic diffractive profile, yet to have the echelettes of the diffractive profile direct light to the same distance foci, a refractive profile may be utilized to vary a distance focus of the echelettes of the diffractive profile. The diffractive profile may include at least one echelette having a power and having a different width in r-squared space than another echelette of the diffractive profile, and being configured to distribute light to a distance focus. The refractive profile may have a refractive zone with a width corresponding to a width of the at least one echelette and having a power that is negative or positive with respect to the power of the at least one echelette, and configured to vary a distance focus of the at least one echelette.

Figure 12:
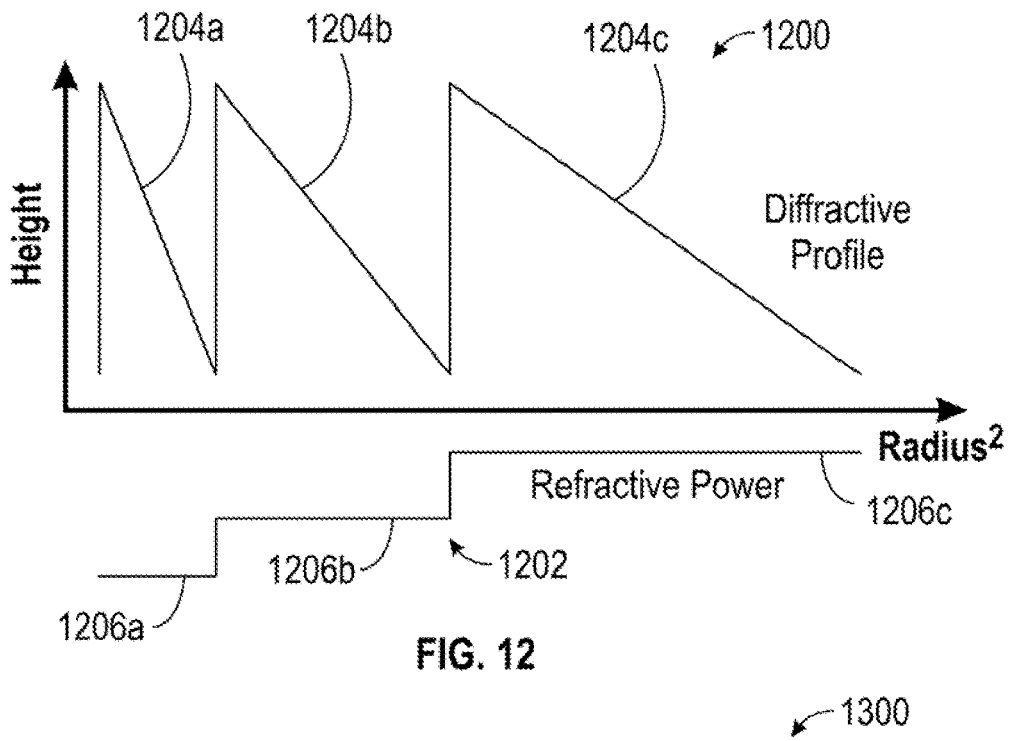
FIG. 12 illustrates a profile of an optic including a diffractive profile and having a plurality of refractive zones.

FIG. 12, for example, illustrates a profile of such an optic, including a diffractive profile 1200 and a refractive profile 1202. The diffractive profile 1200 may be configured as an aperiodic profile, and may be configured similarly as the profile 800 shown in FIG. 8 in embodiments. For example, the profile 1200 may include at least one set of echelettes 1204a-c that may repeat upon the optic (although not shown in FIG. 12, the echelettes 1204a-c may repeat upon the optic in a similar manner as shown in FIG. 8, e.g., once or twice, or a greater number of repetitions). In embodiments, the profile 1200 may include at least one set of echelettes that includes at least two echelettes and repeats upon the optic. In embodiments, a set may include at least three echelettes. In embodiments, the profile may be configured similarly as the profile 700 shown in FIG. 7 and may include a set that does not repeat upon the optic, or may have another profile. The diffractive profile may include at least one echelette having a power and having a different width in r-squared space than another echelette of the diffractive profile, and being configured to distribute light to a distance focus.

The diffractive profile 1200 may be configured in embodiments such that the echelettes 1204a-c each have corresponding diffractive powers between 1 and 2 diopters. In embodiments, other powers may be utilized for the echelettes 1204a-c. For example, in embodiments the corresponding diffractive powers may be between 1 and 3 diopters, or other powers as desired.

The refractive profile 1202 may be a multi-zonal profile and may include a plurality of refractive zones 1206a-c. Each refractive zone 1206a-c may have a width that corresponds to the width of a respective one of the echelettes 1204a-c, and may match the width as shown in FIG. 12 for example. Each refractive zone 1206a-c may have a power that is negative with respect to the power of the respective one of the echelettes 1204a-c. For example, if an echelette 1204c has a corresponding diffractive power of 1.5 diopters, the corresponding refractive zone 1206c may have a power of negative 1.5 diopters. In embodiments, each refractive zone 1206a-c may have a power that is positive with respect to the power of the respective one of the echelettes 1204a-c (e.g, either positive or negative). In embodiments, each refractive zone 1206a-c may be configured to have a power that counteracts the power of the corresponding one of the echelettes 1204a-c. In embodiments, each refractive zone 1206a-c may be configured to have a power that does not counteract the power of the corresponding one of the echelettes 1204a-c.

Each refractive zone 1206a-c may vary the distance focus of the corresponding echelette 1204a-c. In this manner, the correction of longitudinal chromatic aberration provided by the aperiodic diffractive profile 1200 may be achieved, while the distance focus of the echelettes 1204a-c may be the same.

Further, in embodiments herein in which a set of echelettes 1204a-c repeats, the refractive zones of the refractive profile 1202 may repeat, corresponding to the repeating echelettes 1204a-c of the diffractive profile 1200.

In some embodiments, the refractive profile 1202 may be positioned on an opposite optical surface of the optic, with each zone of the refractive profile 1202 positioned optically aligned with a corresponding one of the echelettes 1204a-c. In other embodiments, the refractive profile 1202 may be positioned on the same optical surface as the diffractive profile 1200.

The diffractive profile 1200 and refractive profile 1202 may extend along the optic from the optical axis outward, and may cover the entire pupillary zone of the optic. The optic may have a spatially varying amount of chromatic aberration correction, and may have an amount of longitudinal chromatic aberration correction that differs spatially from the optical axis outward towards the outer periphery of the optic. The amount of longitudinal chromatic aberration may differ over the pupil.

In embodiments, the diffractive profile and refractive profile may cover only a portion of the pupillary zone of the optic. For example, in an embodiment including a diffractive profile 700 such as shown in FIG. 7, in which a refractive profile is positioned at the peripheral zone 712 of the optic, a multizonal refractive profile 1202 as shown may not be utilized at the peripheral zone 712.

In embodiments, utilizing a multizonal refractive profile as disclosed may improve distance modulation transfer function (MTF) by, e.g., 15% for a 3 millimeter pupil and 30% for a 5 millimeter pupil, if diffractive powers of the diffractive profile 1200 are in the range of 1-3 diopter.

The optical or clinical behavior of the embodiments enclosed herein may characterized by a multifocal behavior or by and extended depth of focus behavior, or by a combination thereof. In all of these cases, the embodiments provide patients with an extended range of vision, being larger than that obtain with standard monofocal lenses.

In embodiments, longitudinal chromatic aberration may be reduced by combining two lens materials having different Abbe numbers. Such a doublet may be combined with an aperiodic diffractive profile as disclosed herein.

An optic for an ophthalmic lens that includes a diffractive profile or refractive profile disclosed herein may be fabricated utilizing a variety of methods. A method may include determining optical aberrations of a patient's eye. Measurements of a patient's eye may be made in a clinical setting, such as by an optometrist, ophthalmologist, or other medical or optical professional. The measurements may be made via manifest refraction, autorefraction, tomography, or a combination of these methods or other measurement methods. The optical aberrations of the patient's eye may be determined.

A determination of the visual range of the patient may also be determined. For example, the ability of the patient to focus on near objects (presbyopia) may be measured and determined. A range of corresponding diffractive powers for the ophthalmic lens may be determined.

The measurements of the patient's eye may be placed in an ophthalmic lens prescription, which includes features of an optic that are intended to address the optical aberrations of the patient's eye, as well as features that address the visual range for the patient (e.g., an amount of corresponding diffractive power, a number of focuses, or a range of vision to be provided by the optic).

The ophthalmic lens prescription may be utilized to fabricate an optic for the ophthalmic lens. A refractive profile of the optic may be determined based on the ophthalmic lens prescription, to correct for the optical aberrations of the patient's eye. Such a refractive profile may be applied to the optic, whether on a surface including the diffractive profile or on an opposite optical surface. The diffractive profile may also be determined to provide for the desired distribution of corresponding diffractive powers for the optic.

The determination of one or more of a refractive or diffractive profile and the fabrication of the optic may be performed remotely from the optometrist, ophthalmologist, or other medical or optical professional that performed the measurements of a patient's eye, or may be performed in the same clinical facility of such an individual. If performed remotely, the fabricated optic may be delivered to an optometrist, ophthalmologist, or other medical or optical professional, for being provided to a patient. For an intraocular lens, the fabricated optic may be provided for implant into a patient's eye.

The fabricated optic may be a custom optic fabricated specifically for the patient's eye, or may be fabricated in a manufacturing assembly and then selected by an optometrist, ophthalmologist, or other medical or optical professional for supply to a patient, which may include implantation in the patient's eye.

Figure 13:
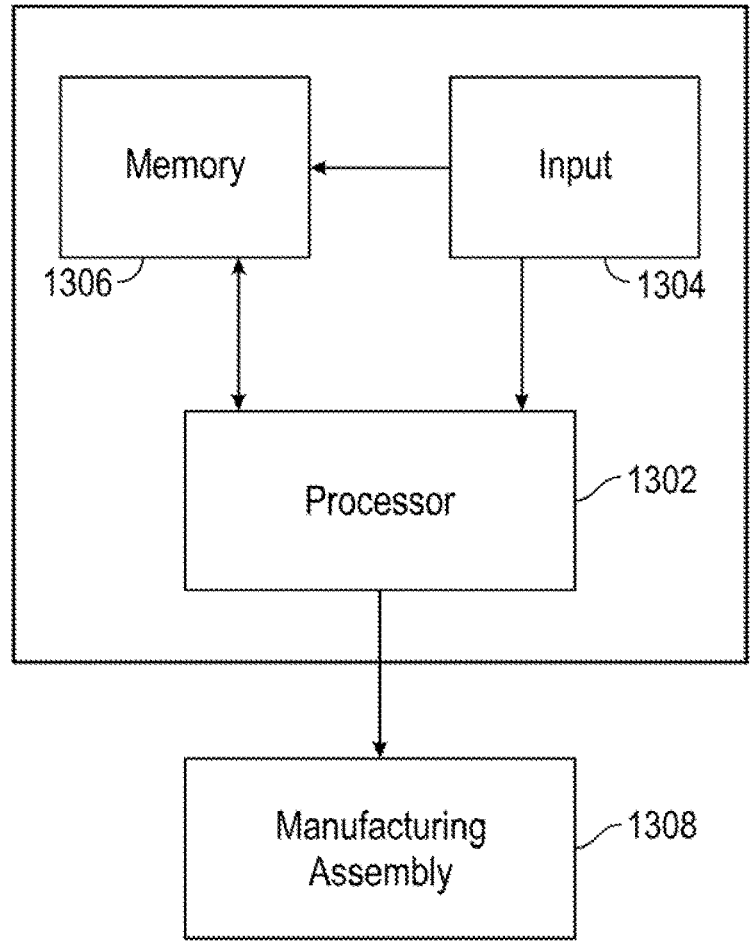
FIG. 13 illustrates an embodiment of a system.

FIG. 13 illustrates an embodiment of a system 1300 that may be utilized to perform all ora portion of the methods disclosed herein. The system 1300 may include a processor 1302, an input 1304, and a memory 1306. In certain embodiments the system 1300 may include a manufacturing assembly 1308.

The processor 1302 may comprise a central processing unit (CPU) or other form of processor. In certain embodiments the processor 1302 may comprise one or more processors. The processor 1302 may include one or more processors that are distributed in certain embodiments, for example, the processor 1302 may be positioned remote from other components of the system 1300 or may be utilized in a cloud computing environment. The memory 1306 may comprise a memory that is readable by the processor 1302. The memory 1306 may store instructions, or features of intraocular lenses, or other parameters that may be utilized by the processor 1302 to perform the methods disclosed herein. The memory 1306 may comprise a hard disk, read-only memory (ROM), random access memory (RAM) or other form of non-transient medium for storing data. The input 1304 may comprise a port, terminal, physical input device, or other form of input. The port or terminal may comprise a physical port or terminal or an electronic port or terminal. The port may comprise a wired or wireless communication device in certain embodiments. The physical input device may comprise a keyboard, touchscreen, keypad, pointer device, or other form of physical input device. The input 1304 may be configured to provide an input to the processor 1302.

The system 1300 may be utilized to perform the methods disclosed herein, such as the processes of determining a diffractive profile of the optic, as well as a refractive profile of the optic. The processor 1302 may be configured to determine the diffractive profile to provide for various corresponding diffractive powers for the optic, as well as determining a refractive profile to correct for ocular aberrations of the patient.

The processor 1302 may provide the refractive profile and/or diffractive profile to the manufacturing assembly 1308, which may be configured to fabricate the optic for the ophthalmic lens based on the refractive profile and/or diffractive profile. The manufacturing assembly 1308 may comprise one or more apparatuses for forming the optic, and may comprise a high volume manufacturing assembly or a low volume manufacturing assembly. The manufacturing assembly 1308 may be used for manufacture remote to a clinic in which measurements of the individual's eye or made, or local to such a clinic. The manufacturing assembly may include apparatuses such as lathe tools, or other lens formation devices to fabricate the optic.

In one embodiment, the processor 1302 may be provided with an ophthalmic lens prescription for the individual's eye that may be provided as discussed herein. The processor 1302 may receive the ophthalmic lens via the input 1304. The system 1300 may fabricate the optic for the ophthalmic lens based on the prescription.

The system 1300 may be configured to fabricate any of the embodiments of ophthalmic lenses disclosed herein.

In one embodiment, a diffractive profile such as the profile 700, profile 800, profile 1000, profile 1100, or profile 1200 may be positioned on a surface of a lens that is opposite an aspheric surface. The aspheric surface on the opposite side of the lens may be designed to reduce corneal spherical aberration of the patient.

In one embodiment, one or both surfaces of the lens may be aspherical, or include a refractive surface designed to extend the depth of focus, or create multifocality.

In one embodiment, a refractive zone on one or both surfaces of the lens may be utilized that may be the same size or different in size as one of the diffractive zones. The refractive zone includes a refractive surface designed to extend the depth of focus, or create multifocality.

Any of the embodiments of lens profiles discussed herein may be apodized to produce a desired result. The apodization may result in the step heights and step offsets of the echelettes being gradually varied according to the apodization, as to gradually increasing the amount of light in the distance focus as a function of pupil diameter.

The features of the optics disclosed herein may be utilized by themselves, or in combination with refractive profiles of the optics and/or with features providing for correction of chromatic aberrations (e.g., achromats, which may be diffractive).

The ophthalmic lenses disclosed herein in the form of intraocular lenses are not limited to lenses for placement in the individual's capsular bag. For example, the intraocular lenses may comprise those positioned within the anterior chamber of the eye. In certain embodiments the intraocular lenses may comprise "piggy back" lenses or other forms of supplemental intraocular lenses.

Features of embodiments may be modified, substituted, excluded, or combined as desired.

In addition, the methods herein are not limited to the methods specifically described, and may include methods of utilizing the systems and apparatuses disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An ophthalmic lens comprising:
   an optic including a first surface and a second surface each disposed about an optical axis and extending radially outward from the optical axis to an outer periphery of the optic, the first surface facing opposite the second surface, and
   the optic including a plurality of echelettes disposed on the first surface between the optical axis and the outer periphery of the optic, each of the plurality of echelettes having a different width in r-squared space than any other echelette on the first surface between the optical axis and the outer periphery of the optic,
   wherein the optic includes a central zone and a peripheral zone, and the plurality of echelettes are positioned on the central zone, and the peripheral zone includes a refractive surface,
   wherein at least two of the echelettes of the plurality of echelettes have a different step height,
   wherein the plurality of echelettes define at least one set of echelettes, and the at least one set of echelettes repeating at least once upon the central zone of the optic,
   wherein the refractive surface is adjacent to the plurality of echelettes, and extends radially outward from the plurality of echelettes to the outer periphery of the optic,
   wherein the plurality of echelettes provide an extended depth of focus.

2. The ophthalmic lens of claim 1, wherein the plurality of echelettes includes at least three echelettes.

3. The ophthalmic lens of claim 1, wherein the plurality of echelettes includes at least four echelettes.

4. The ophthalmic lens of claim 1, wherein the plurality of echelettes includes at least five echelettes.

5. The ophthalmic lens of claim 1, wherein at least one echelette of the plurality of echelettes is configured to distribute light to a near focus or to an intermediate focus.

6. The ophthalmic lens of claim 1, wherein the plurality of echelettes modify chromatic aberration in a distance focus.

7. The ophthalmic lens of claim 1, wherein the refractive surface provides one or more of an intermediate focus, a near focus, or an extended depth of focus.

8. The ophthalmic lens of claim 1, wherein the optical axis of the optic passes through the central zone.

9. The ophthalmic lens of claim 1, wherein at least one of the plurality of echelettes is configured to distribute light to a near focus.

10. The ophthalmic lens of claim 9, wherein at least one of the plurality of echelettes is configured to distribute light to an intermediate focus.

11. The ophthalmic lens of claim 10, wherein each echelette is configured to distribute light to a distance focus.

12. The ophthalmic lens of claim 1, wherein each echelette of the plurality of echelettes is positioned adjacent to another echelette of the plurality of echelettes.

* * * * *